United States Patent
Soll et al.

(10) Patent No.: US 9,949,953 B2
(45) Date of Patent: *Apr. 24, 2018

(54) TOPICAL COMPOSITIONS COMPRISING FIPRONIL AND PERMETHRIN AND METHODS OF USE

(71) Applicant: MERIAL, INC., Duluth, GA (US)

(72) Inventors: Mark David Soll, Alpharetta, GA (US); James Pate, Hampton, NJ (US); Lisa A. Baker, Somerset, NJ (US)

(73) Assignee: MERIAL INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/248,327

(22) Filed: Aug. 26, 2016

(65) Prior Publication Data
US 2016/0361297 A1    Dec. 15, 2016

Related U.S. Application Data

(63) Continuation of application No. 13/774,159, filed on Feb. 22, 2013, now Pat. No. 9,457,088.

(60) Provisional application No. 61/602,472, filed on Feb. 23, 2012.

(51) Int. Cl.
| | | |
|---|---|---|
| A61K 31/415 | (2006.01) | |
| A61K 31/215 | (2006.01) | |
| A61K 45/06 | (2006.01) | |
| A61K 47/14 | (2017.01) | |
| A61K 47/22 | (2006.01) | |
| A01N 53/00 | (2006.01) | |
| A61K 9/00 | (2006.01) | |
| A61K 47/08 | (2006.01) | |
| A61K 47/18 | (2017.01) | |
| A01N 47/02 | (2006.01) | |
| A01N 25/02 | (2006.01) | |
| A01N 37/38 | (2006.01) | |
| A01N 43/40 | (2006.01) | |
| A01N 43/56 | (2006.01) | |
| A01N 49/00 | (2006.01) | |
| A61K 31/201 | (2006.01) | |
| A61K 31/216 | (2006.01) | |
| A61K 31/4402 | (2006.01) | |
| A61K 47/10 | (2017.01) | |
| A61K 47/44 | (2017.01) | |

(52) U.S. Cl.
CPC ............ *A61K 31/415* (2013.01); *A01N 25/02* (2013.01); *A01N 37/38* (2013.01); *A01N 43/40* (2013.01); *A01N 43/56* (2013.01); *A01N 47/02* (2013.01); *A01N 49/00* (2013.01); *A01N 53/00* (2013.01); *A61K 9/0017* (2013.01); *A61K 31/201* (2013.01); *A61K 31/215* (2013.01); *A61K 31/216* (2013.01); *A61K 31/4402* (2013.01); *A61K 45/06* (2013.01); *A61K 47/08* (2013.01); *A61K 47/10* (2013.01); *A61K 47/14* (2013.01); *A61K 47/18* (2013.01); *A61K 47/22* (2013.01); *A61K 47/44* (2013.01)

(58) Field of Classification Search
None
See application file for complete search history.

(56) References Cited

U.S. PATENT DOCUMENTS

| 4,902,510 A | 2/1990 | Garden |
| 6,001,858 A | 12/1999 | Sirinyan et al. |
| 6,010,710 A | 1/2000 | Etchegaray |
| 6,096,329 A | 8/2000 | Jeannin |

(Continued)

FOREIGN PATENT DOCUMENTS

| AU | 200043947 | 10/2000 |
| AU | 2002338201 B2 | 5/2003 |

(Continued)

OTHER PUBLICATIONS

"Efficacy and Degradation of Fipronil Applied to Cotton for Control of Anthonomus grandis grandis (Coleoptera: Curculionidae)", Joseph E. Mulrooney and Deepa Goli, Journal of Economic Entomology, 1999, vol. 92(6), 1364-1368).

(Continued)

*Primary Examiner* — James H Alstrum-Acevedo
*Assistant Examiner* — Dale R Miller
(74) *Attorney, Agent, or Firm* — Judy Jarecki-Black; John Ezcurra; Merial, Inc.

(57) ABSTRACT

The subject matter disclosed herein is directed to stable, highly-effective topical formulations comprising permethrin, fipronil and a solvent system that is sufficient to solubilize these two active ingredients and limit degradation of fipronil to its sulfone, and their uses in topical applications on animals and the environment. Useful formulations comprise from about 30% to about 55% (w/w) permethrin and about 2 to 15% (w/w) fipronil and a solvent system that comprises N-methyl pyrrolidone and a glycol, glycol ether, glycol ester, fatty acid ester or neutral oil, wherein the N-methyl pyrrolidone and glycol, glycol ether, glycol ester, fatty acid ester or neutral oil are present in a weight:weight ratio of from about 1:2.0 to about 1:3.5, glycol, glycol ether, glycol ester, fatty acid ester or neutral oil to n-methyl pyrrolidone. These two actives when combined in the described amounts have been found to have unexpected enhanced repellent activity against stable fly. However, it is the formulations described herein that provide solvency and stability that maintain synergistic concentrations after application on an animal.

27 Claims, 5 Drawing Sheets

(56) References Cited

U.S. PATENT DOCUMENTS

| | | | |
|---|---|---|---|
| 6,395,765 B1 | 5/2002 | Etchegaray | |
| 6,806,292 B2 | 10/2004 | Sirinyan et al. | |
| 7,025,978 B1 | 11/2006 | Sirinyan et al. | |
| 7,262,214 B2 * | 8/2007 | Soll | A01N 25/002 424/405 |
| 7,906,535 B2 * | 3/2011 | Cottrell | A01N 25/34 514/345 |
| 2002/0081327 A1 | 6/2002 | Etchegaray et al. | |
| 2002/0103233 A1 | 8/2002 | Arther | |
| 2004/0161441 A1 | 8/2004 | Sirinyan et al. | |
| 2006/0025728 A1 | 11/2006 | Sirinyan et al. | |
| 2009/0017084 A9 | 1/2009 | Sirinyan et al. | |
| 2010/0016398 A1 | 1/2010 | Sirinyan et al. | |
| 2011/0071193 A1 | 2/2011 | Nouvel | |

FOREIGN PATENT DOCUMENTS

| | | |
|---|---|---|
| AU | 2004237454 B2 | 11/2004 |
| AU | 2004290502 C1 | 6/2005 |
| AU | 2006201364 B2 | 4/2006 |
| AU | 2007341647 B2 | 7/2008 |
| EP | 1013170 A1 | 6/2000 |
| GB | 2334888 A | 8/1999 |
| GB | 2396557 A | 6/2004 |
| RU | 2340181 C1 | 12/2008 |
| WO | 95/22902 A1 | 8/1995 |
| WO | 96/16543 | 6/1996 |
| WO | 99/47139 A1 | 9/1999 |
| WO | 03/015519 A1 | 2/2003 |
| WO | 2005/058038 A1 | 6/2005 |
| WO | 2005/085211 A1 | 9/2005 |

OTHER PUBLICATIONS

Australian Pesticides and Veterinary Medicines Authority database abstract for Advantix for Dogs 4-10 kg (Registration No. 58261).
Summary of Product Characteristics and Post Authorization Assessments for Advantix for Dogs 4-10 kg from the U.K. Veterinary Medicines Directorate website; revised Dec. 2011; date of first authorization Dec. 23, 2003.
Registration extract for Frontline Spot-on Dog from the Irish Medicines Board website.
Summary of Product Characteristics for Frontline Spot-on Dog. Irish Medicines Board; date of revision of text Nov. 13, 2008.
Australian Pesticides and Veterinary Medicines Authority database abstract for Frontline Top Spot for small dog (Registration No. 48606).
Summary of Product Characteristics for Advantage 40 Spot-on solution for Cats. Irish Medicines Board; date of first authorization Aug. 7, 2007; date of revision of text Mar. 23, 2011.
Australian Pesticides and Veterinary Medicines Authority database abstract for Advantage for Dogs 4-10 kg (Registration No. 50398).
MSDS for Frontline Top Spot, Merial Limited, Oct. 23, 2001.
MSDS for Advantix for Dogs, Bayer Healthcare, Feb. 7, 2007.

* cited by examiner

TOPICAL COMPOSITIONS COMPRISING FIPRONIL AND PERMETHRIN AND METHODS OF USE

CROSS REFERENCE TO RELATED APPLICATIONS

This application is a continuation of U.S. patent application Ser. No. 13/774,159 filed Feb. 22, 2016, which claims the benefit of priority to U.S. Provisional Patent Application No. 61/602,472, filed 23 Feb. 2012, both incorporated herein by reference in their entirety.

FIELD OF THE INVENTION

The subject matter disclosed herein is directed to pharmaceutical and veterinary formulations that provide an unexpected enhanced repellant activity and superior parasiticidal efficacy. The solvent system of the formulations provide excellent solvency and reduce the amount of fipronil sulfone formation over a wide range of conditions.

BACKGROUND OF THE INVENTION

Animals, such as mammals and birds are often susceptible to parasite infestations. These parasites may be ectoparasites, such as fleas, ticks, mosquitoes, mites, flies, sand flies and lice and endoparasites such as roundworms, hookworms, flukes and heartworms. Domesticated animals including farm animals are particularly susceptible to parasite infections and infestations.

Parasitic diseases may be caused by either endoparasites or ectoparasites. Endoparasites refer to those parasites living inside the body of the host (such as in the stomach, lungs, heart, intestines, etc.). Ectoparasites are those parasites that live on the outer surface of the host but still draw nutrients from the host. Endoparasitic infections may further be subdivided based on class of parasite involved in the infection. These parasitic infections and infestations are often associated with illness and death or reduced productivity.

Examples of endoparasites which infect animals include but are not limited to gastro-intestinal parasites of the genera *Ancylostoma, Necator, Ascaris, Strongyloides, Trichinella, Capillaria, Toxocara, Toxascaris, Trichuris, Enterobius, Haemonchus, Trichostrongylus, Ostertagia, Cooperia, Oesophagostomum, Bunostomum, Strongylus, Cyathostomum* and *Parascaris* among others, and those that are found in the blood vessels or other tissues and organs include *Wuchereria, Brugia, Onchocerca, Dirofilaria* and the extra-intestinal stages of *Strongyloides, Toxocara* and *Trichinella*.

Ectoparasites which infest man and domestic animals include arthropods, such as ticks, fleas, mites, mosquitoes, lice, and the like and infestations by these parasites can result in transmission of pathogens that can cause serious and even fatal diseases.

Infestations by ectoparasitic arthropods including but not limited to ticks, mites, lice, stable flies, horn flies, blowflies, face flies, fleas, mosquitoes and the like are also a serious problem. Infestation by these parasites may result not only in loss of blood and skin lesions, but also can interfere with normal eating habits thus causing weight loss. Ectoparasitic infestations of a host can also result in transmission of pathogenic agents that cause serious diseases including but not limited to encephalitis, anaplasmosis, Babesiosis, Rocky Mountain spotted fever, Lyme disease, ehrlichiosis, West Nile virus, swine pox, malaria, yellow fever, and others, many of which can be fatal to the host. Animals may be infected by several species of parasites at the same time since infection by one parasite may weaken the animal and make it more susceptible to infection by a second species of parasites.

A parasite which is prevalent among domesticated animals is *Stomoxys calcitrans* (stable fly). Stable flies will feed on blood from practically any warm blooded animal, including humans, pets, and livestock. During periods of high stable fly activity, humans can be severely annoyed and this insect has been called the biting house fly. Individual flies may feed more than once per day. Peaks of feeding activity commonly occur during the early morning and again in the late afternoon. Stable flies prefer feeding on lower parts of the hosts such as the legs.

Both male and female stable flies feed on blood. The female requires blood meals to produce viable eggs. Females deposit their eggs in a variety of decaying animal and plant wastes. Stable flies breed in soggy hay, grasses or feed, piles of moist fermenting weed or grass cuttings, spilled green chop, peanut litter, and seaweed deposits among beaches, in soiled straw bedding and sometimes in hay ring feeding sites. Each female fly may lay 500-600 eggs in 4 separate batches. Eggs hatch in 2-5 days into larvae which feed and mature in 14-26 days. The average life cycle is 28 days, ranging from 22-58 days, depending on the weather conditions.

Farm animals can be severely affected by the stable fly. Since the fly takes blood meals, animals are weakened from blood loss and continual irritation. Animals such as swine, cattle, and horses infested with stable flies may show reduced weight gains, among other harmful effects. While one stable fly does not cause significant damage, 50-100 of these blood-sucking pests together with 500 horn flies cause a significant loss of blood. This can result in a significant loss of milk and beef production from animals each year.

Another important parasite is the tick genus *Rhipicephalus*, especially those of the species *microplus* (cattle tick), *decoloratus* and *annulatus*. Ticks, such as *Rhipicephalus microplus*, are particularly difficult to control because they live in the pasture where the farm animals graze. Other important parasites of cattle and sheep are listed as follows: myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). These are flies whose larva constitute the animal parasite; flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*.

More prevalent among domesticated animals, such as cats and dogs, are the following ectoparasites: cat and dog fleas (*Ctenocephalides felis, C. canis*. and the like), ticks (*Rhipicephalus* spp., *Ixodes* spp., *Dermacentor* spp., *Amblyoma* spp. and the like), and mites (*Demodex* spp., *Sarcoptes* spp., *Cheyletiella* spp., *Otodectes* spp. and the like), lice (*Trichodectes* spp., Lignonathus spp., and the like), mosquitoes (*Aedes* spp., *Culex* spp., *Anopheles* spp., and the like) and flies (*Hematobia* spp., *Musca* spp., *Stomoxys* spp., *Dermatobia* sp., *Cochliomyia* spp., and the like).

Fleas are a particular problem because not only do they adversely affect the health of the animal or human, but they also cause a great deal of psychological stress. Moreover, fleas are also vectors of pathogenic agents in animals, such as dog tapeworm (*Thpylidium caninum*), and humans.

Similarly, ticks are also harmful to the physical and psychological health of the animal. However, the most serious problem associated with ticks is that they are the vector of pathogenic agents, agents which cause diseases in both humans and animals. Major diseases which are caused by ticks include borrelioses (Lyme disease caused by *Borrelia burgdorferi*), Babesioses (or piroplasmoses caused by *Babesia* sp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

The above list is not exhaustive and other ectoparasites are well known in the art to be harmful to animals and humans.

While it is known in the art that it is sometimes possible to combine various parasiticides in order to broaden the parasiticidal spectrum, it is not possible to predict, a priori, with any reasonable certainty which combinations will work for a particular animal or disease state. For this reason, the results of various combinations are not always successful and there is a need in the art for more effective formulations which may be easily administered to the animal and have the required solvency, stability and bioavailability.

Formulations comprising different actives are especially difficult to successfully formulate because of the challenges in achieving the required solvency, stability and bioavailability. Thus, there is a need in the art for combination antiparasitic formulations that meet the required solvency, stability and bioavailability of the parasiticides to be formulated therein.

SUMMARY OF THE INVENTION

The subject matter disclosed herein is directed to stable, highly-effective topical formulations comprising a pyrethroid, such as permethrin, a N-arylpyrazole, such as fipronil and a solvent system that is sufficient to solubilize these two active ingredients and limit the oxidation of fipronil to fipronil sulfone, but that is safe for topical application. In one embodiment, the topical formulation is in the form of a spot-on formulation. In another embodiment, the topical formulation is in the form of a pour-on formulation. In one embodiment, formulations comprise about 30 to about 55% (w/w) permethrin and about 2 to 15% (w/w) fipronil and a solvent system that comprises N-methyl pyrrolidone (NMP) and a glycol, glycol ether, glycol ester, fatty acid ester or neutral oil. In some embodiments, the formulations of the invention comprise at least about 40% (w/w) permethrin and at least about 5% (w/w) fipronil in a solvent system comprising NMP and a glycol, glycol ether, glycol ester, fatty acid ester or neutral oil, wherein the NMP and glycol, glycol ether, glycol ester, fatty acid ester or neutral oil are present in a ratio of from about 1:2.0 to about 1:3.5 (weight:weight), glycol, glycol ether, glycol ester, fatty acid ester or neutral oil to NMP. In other embodiments, the ratio of glycol, glycol ether, glycol ester, fatty acid ester or neutral oil to NMP is about 1:2.0 to about 1:3.0, about 1:2.5 to about 1:3.5, or about 1:2.5 to about 1:3.0 (weight:weight).

These two actives when combined in the described amounts in the solvents described herein have been found to have excellent parasiticidal activity and unexpected enhanced repellency against stable flies. However, it is the particular combination of solvents in the formulations described herein that provide the required solvency and physical stability and limit the oxidation of fipronil to its sulfone that maintain concentrations of the actives that result in the unexpected enhanced repellency and superior efficacy against stable flies after application on an animal. Additionally, as described herein, the selection of the diluent to be combined with NMP is critical to limiting the oxidation of fipronil to fipronil sulfone in the formulations and maintaining effective concentrations.

In some embodiments of the invention, additional active agents may be combined in the topical formulations comprising fipronil and permethrin. The additional active agents include, but are not limited to, an avermectin, a milbemycin, a spinosyn, a spinosoid, a benzimidazole, levamisole, pyrantel, morantel, praziquantel, closantel, clorsulon, an amino acetonitrile active agent, an insect growth regulator, a neonicotinoids or an aryloazol-2-yl cyanoethylamino active agent, or a combination of thereof.

The subject matter disclosed herein is also directed to methods of use of the formulations to combat infestations of ectoparasites, including, but not limited to, fleas, ticks, mosquitoes, and various types of parasitic flies, such as stable flies, on or around mammals or birds and in the environments where they reside. The methods comprise administering an effective amount of a formulation described herein, in particular a spot-on or pour-on formulation, to the mammal or bird. Animals include mammals, such as dogs, zebras and horses, cattle, pigs, yaks, rodents, deer, goats, sheep and llamas and birds, such as chickens, turkeys and quail. Environments include animal houses, such as dog bedding, horse stables and chicken litter.

The present subject matter is also directed to a method of preparing the compositions described herein. The method comprises contacting one or both of the actives with one or more of the solvents selected from N-methyl pyrrolidone and a glycol, glycol ether, glycol ester, fatty acid ester or neutral oil, wherein the final formulation contains N-methyl pyrrolidone and glycol, glycol ether, glycol ester, fatty acid ester or neutral oil. In one embodiment, the glycol, glycol ether, glycol ester, fatty acid ester or neutral oil and NMP are combined in a ratio of from about 1:2.0 to about 1:3.5, about 1:2.0 to about 1:3.0, about 1:2.5 to about 1:3.5, or about 1:2.5 to about 1:3.0 (weight:weight), glycol, glycol ether, glycol ester, fatty acid ester or neutral oil to NMP. The formulations described herein are stable and exhibit unexpected enhanced repellency and efficacy against stable flies.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
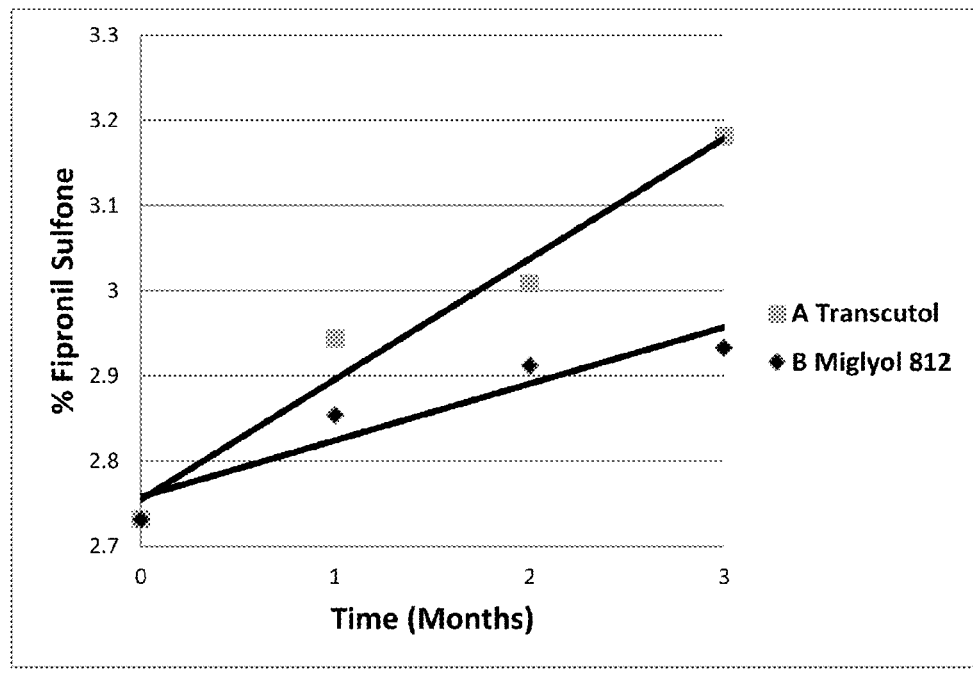
FIG. 1 depicts sulfone formation at 50° C. for formulations containing N-methylpyrrolidone (NMP) and diethyleneglycol monoethyl ether (DGME, TRANSCUTOL®) or MIGLYOL® 812 (a neutral oil). The data show that the DGME-containing formulation contains more than 10% higher concentration of fipronil sulfone compared to the neutral oil-containing formulation. Each formulation contains about 6% (w/w) fipronil, 45% (w/w) permethrin and 33% (w/w) NMP. Formulation A contains (DGME), QS to 100% (~14-15% w/w); formulation B contains MIGLYOL® 812, QS to 100% (~14-15% w/w). The formulations in this study do not contain an added antioxidant.
Figure 2:
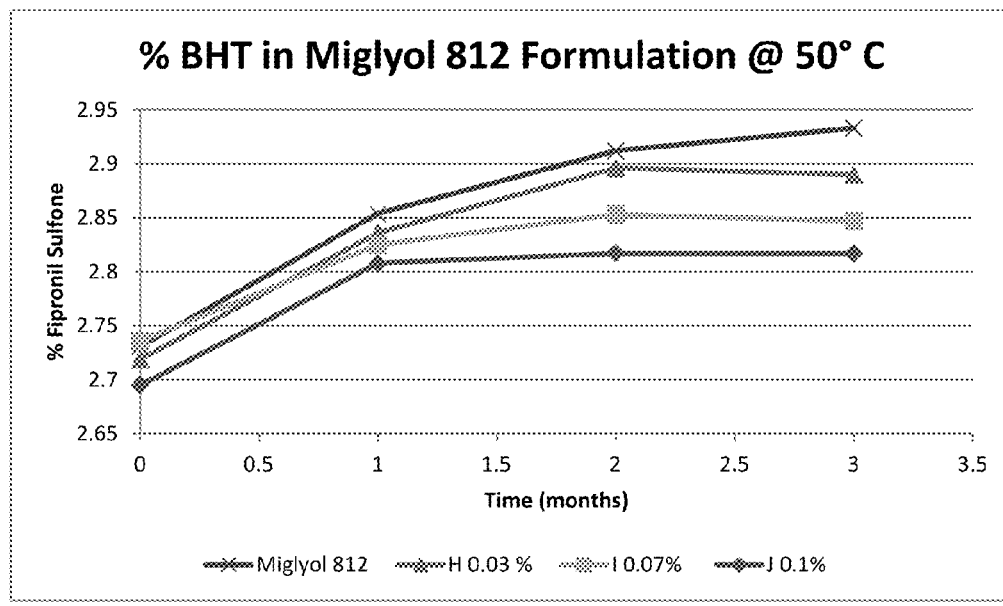
FIG. 2 depicts formulations which all contain MIGLYOL® 812 and either no antioxidant or a different level of antioxidant. The data show that all formulations have fipronil sulfone levels below about 2.950%. The formulation containing 0.10% BHT has a fipronil sulfone level of about 2.800%.

The presently disclosed subject matter will be described more fully herein. However, many modifications and other embodiments of the presently disclosed subject matter set forth herein will come to mind to one skilled in the art to which the presently disclosed subject matter pertains having the benefit of the teachings presented in the foregoing description. Therefore, it is to be understood that the presently disclosed subject matter is not to be limited to the specific embodiments disclosed and that modifications and other embodiments are intended to be included within the scope of the appended claims.

It is well-known that formulating an active into a spot-on or pour-on formulation is challenging. Even more challenging is successfully formulating two different actives into a composition, whereby both actives remain in solution and are available in the desired amounts. Since it has been shown herein that the combination has an unexpected enhanced repellency against stable flies, it is critical that the formulation provide the required solubility and physical and chemical stability to ensure that the concentrations resulting in enhanced repellency are maintained even after administration of the formulation to the animal.

Disclosed herein is a unique combination of a solvent system for use with the combination of permethrin and fipronil, whereby the formulation components are present in specified ranges and particular ratios relative to one another. Such enumerated ratios are not broadly generalized amounts, but are specific values of effective ranges and ratios for fipronil and permethrin. Advantageously, the solvent systems described herein solubilize a high concentration of permethrin and are compatible with fipronil. Consequently, the actives stay in solution, are not substantially degraded and are available to combat pest infestations at effective concentrations at the loci where infestations can occur. As used herein, the term "physical stability" and "physically stable" refers to a property of a formulation wherein no significant amount permethrin or fipronil crystals form at low temperatures (including −20° C., 4° C. and 10° C.), the active ingredients remain in solution even after application. The physical stability of the compositions may be described in terms of crystal formation when the formulation is stored at a particular temperature for a period of days, weeks, months or even years. The solvent system also provides the required safety profile for its intended uses.

Formulations that contain permethrin and an additional active ingredient often suffer from physical instability. Permethrin, especially in high concentrations above 20% (w/w), tends to form crystals in the formulation. When a second active is added to the formulation, the physical instability problems can increase exponentially since the physical properties and requirements for formulation of an additional ingredient must also be considered. The second preferred active disclosed herein is fipronil. However, when fipronil is combined with N-methylpyrrolidone (NMP), which is an effective solvent for high concentrations of permethrin, significant levels of oxidation of fipronil to fipronil sulfone is observed.

Fipronil sulfone is also a principal in vivo metabolite of fipronil. It has the following structure:

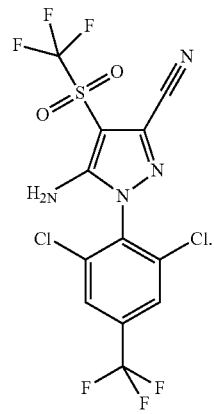 [SMILES: N#Cc1nn(-c2c(Cl)cc(C(F)(F)F)cc2Cl)c(N)c1S(=O)(=O)C(F)(F)F]

Fipronil used to prepare the formulations can contain fipronil sulfone at the time of formulation. In other words, it is possible that useful grades of fipronil have some amount of fipronil sulfone already present as a byproduct of its preparation. In one embodiment fipronil has below about 3.5% fipronil sulfone at the time of formulation with NMP. Some grades of fipronil may have lower levels of fipronil sulfone, even 0%. However, once fipronil is contacted with NMP, it is believed that fipronil sulfone may continue to form in solution. Further, it is significantly more costly to use fipronil that is completely free of fipronil sulfone. However, the formulation described herein advantageously minimize or substantially slow further fipronil sulfone formation compared to formulations with other common solvents used in topical compositions no matter how much is present at the time of formulation.

The solvent system described herein was designed after the finding that fipronil is susceptible to fipronil sulfone formation in the presence of NMP. While not being bound to any particular theory, it is believed that peroxides present in NMP can facilitate the formation of fipronil sulfone. Furthermore, it is known that NMP can generate peroxides in the presence of oxygen (see Drago and Riley, *J. Am. Chem.*

Soc. 1990, 112, 215-218; Reynolds et al., *Journal of Pharmaceutical Sciences*, 2012, 101(2), pp. 761-776). Thus, it has been found that NMP, while a useful solvent, poses technical hurdles when used as a solvent for fipronil in a concentrated topical formulation, such as a spot-on formulation. The oxidation of fipronil in NMP must be addressed since NMP is an effective solvent for permethrin at the concentration levels present in the formulations disclosed herein. However, the required amount of NMP in the formulations of the invention was unexpectedly observed to result in the oxidation of fipronil to fipronil sulfone at levels that were higher than desired.

N-methylpyrrolidone (NMP) is a chemical compound with a 5-membered lactam structure. It is a clear to slightly yellow liquid soluble in water and conventional organic solvents. It is a polar aprotic solvent and a very weak base. Other names for this compound are: 1-methyl-2-pyrrolidone, N-methyl-2-pyrrolidinone, and m-pyrrole, and PHARMASOLVE®. Despite its usefulness, its use for topical application may pose problems for the skilled formulator. In some cases NMP may cause skin irritation, redness or dermatitis. Accordingly, although it is acceptable in topical formulations, it is preferred that the level be as low as possible.

The oxidation of fipronil to fipronil sulfone was observed at higher than desired levels when NMP was diluted with traditional solvents used in combination with fipronil in topical formulations, such as diethyleneglycol monoethyl ether (TRANSCUTOL® or DGME). Diethyleneglycol monoethyl ether is commonly used in many topical formulations and has been found to be a very effective solvent for use in formulating topical fipronil formulations. When DGME and other diluents are used in combination with NMP, the amount of NMP can be reduced so long as the necessary physical properties of the composition remain unaltered. However, it has been found that when NMP is combined with co-solvents normally used with fipronil, such as DGME, fipronil is oxidized to its sulfone at higher than desired rates. Consequently, to minimize the formation of fipronil sulfone, the use of an antioxidant at about 10-times the level of antioxidant that is effective in the formulations described herein was required.

It has been surprisingly found that a solvent system containing NMP in combination with a neutral oil, including MIGLYOL® 812 (caprylic/capric triglyceride), results in significantly lower sulfone formation compared with other solvents typically used in fipronil topical formulations. Neutral oils are known in the art. They are light to colorless liquids of neutral odor and taste.

MIGLYOL®-type neutral oils are clear, slightly yellowish esters of saturated coconut and palm kernel oil-derived caprylic and capric fatty acids and glycerin or propylene glycol. Some neutral oils are triglycerides of fractionated plant fatty acids with chain lengths of $C_8$ to $C_{10}$. Two commercially available products are known as MIGLYOL® 810 and MIGLYOL®812. Another useful neutral oil is a triglyceride of fractionated plant fatty acids with chain lengths of $C_8$ and $C_{10}$ combined with linoleic acid (about 4-5%). A commercially available product is known as MIGLYOL® 818. Another useful neutral oil is a glycerin ester of fractionated plant fatty acids with chain lengths of $C_8$ and $C_{10}$ combined with succinic acid. A commercially available product is known as MIGLYOL® 829. Another useful neutral oil is a propylene glycol diester of saturated plant fatty acids with chain lengths of $C_8$ and $C_{10}$ combined with succinic acid. A commercially available product is known as MIGLYOL® 840 (propylene glycol dicaprylate/dicaprate).

Other fatty acids include stearyl stearate, palmitate, and myristate. Other examples of suitable neutral oils and fatty acid esters include hydrocarbonaceous vegetable oils, such as liquid triglycerides of fatty acids comprising from 4 to 24 carbon atoms (such as triglycerides, heptanoic acid and octanoic acid), sunflower oil, maize oil, soybean oil, gourd oil, grape seed oil, sesame oil, hazelnut oil, apricot oil, macadamia oil, castor oil, avocado oil, jojoba oil and karite butter; synthetic esters, such as synthetic esters of fatty acids such as, for example, purcellin oil, isononyl isononanoate, isopropyl myristate, 2-ethylhexyl palmitate, 2-octyldodecyl stearate, 2-octyldodecyl erucate, and isostearyl isostearate. As described fully herein, the requirement of the diluent is that it does not substantially introduce additional peroxide species into the NMP/co-solvent system. Consequently, fipronil sulfone formation is mitigated and substantially lower levels of antioxidants can be used to yield long-term stability of the permethrin, fipronil combination formulation.

The fipronil/permethrin compositions described herein containing NMP in combination with neutral oils will have significantly less fipronil sulfone growth compared to fipronil/permethrin compositions that use a different NMP/co-solvent system. It is useful that the present compositions inhibit fipronil sulfone formation such that the level of fipronil sulfone present at about 3 months after formulation has not increased by more than about 50% of the original fipronil sulfone present at the time of formulation, e.g., the amount present in neat fipronil raw material, as measured by area % of the fipronil sulfone peak relative to the fipronil peak by HPLC. In one embodiment, the solvent system of the invention inhibit the formation of fipronil sulfone to an extent that at three months after formulation, the fipronil sulfone has not increased by more than about 45% of the original fipronil sulfone present at the time of formulation; or the fipronil sulfone has not increased by more than about 40% of the original fipronil sulfone present at the time of formulation; or the fipronil sulfone has not increased by more than about 35% of the original fipronil sulfone present at the time of formulation; or the fipronil sulfone has not increased by more than about 30% of the original fipronil sulfone present at the time of formulation; or the fipronil sulfone has not increased by more than about 25% of the original fipronil sulfone present at the time of formulation. In another embodiment, at three month after formulation, the fipronil sulfone has not increased by more than about 20% of the original fipronil sulfone present at the time of formulation; or the fipronil sulfone has not increased by more than about 15% of the original fipronil sulfone present at the time of formulation. In yet another embodiment, at three month after formulation, the fipronil sulfone has not increased by more than about 10% of the original fipronil sulfone present at the time of formulation.

The purpose of the antioxidant in the compositions is largely to combat any peroxides found in NMP. It has been found that when a diluent is carefully selected to limit additional introduction of harmful oxidative species, such as peroxide species, into the composition, the amount of antioxidant can be preferably kept at GRAS (generally regarded as safe) levels or substantially lower. In some embodiments, an effective amount of antioxidant is not more than about 0.25% (w/w). In another embodiment, the antioxidant is present at a concentration of not more than about: 0.2% (w/w); 0.19% (w/w); 0.18% (w/w); 0.17% (w/w); 0.16% (w/w); 0.15% (w/w); 0.14% (w/w); 0.13% (w/w); 0.12%

(w/w) or 0.11% (w/w). In still another embodiment, the antioxidant is present at a concentration of not more than about 0.1% (w/w).

Another problem with concentrated topical formulations is that any amount of crystals in the formulation may lead to a concentration of active(s) in the precipitated material that is too high for safe, point-of-application topical use. Further, since precipitation effectively removes active(s) from solution, the concentration of active(s) remaining in solution can be too low, and thus not provide the efficacy described herein. Additionally, once crystals begin to form, they behave as seeds for further crystal formation. This process results in increasing precipitation of components out of the solvent system, and deleterious effects on the concentration of active(s) in the formulation.

It is evident that should one or both of the actives form crystals or otherwise precipitate from the solution either before or after application, the relative amounts of the active agents would be altered. Accordingly, the amounts of actives would be expected to deviate from the amounts required for enhanced repellent activity. Therefore, the property of the present compositions whereby each active remains in solution even after application on the animal also contributes to the enhanced activity against stable flies observed. As reported in WO2007/143298, incorporated herein in its entirety, it is difficult to form a high concentration solution of permethrin. However, the present compositions contain about 30% (w/w) permethrin at the lowest concentration, and in some embodiments contain about 40 to about 45 (w/w). The difficulty of successfully formulating permethrin in these concentrations is exponentially greater when formulating a second, different active. This is especially true if the actives are of different physical properties. Surprisingly, the compositions described herein have been shown to exhibit surprising enhanced repellency and excellent insecticidal efficacy against stable flies when applied to a localized area on an animal. Thus, the enhanced repellency observed would be expected to result from the concentration of each active as the composition spreads over the animal's coat and skin. The unexpected enhanced repellency would not be limited to the loci where the composition is directly applied to the animal, and this is important for effective control of stable flies and other ectoparasites since these ectoparasites will feed on different locations on the animal. The formulations described herein provide effective amounts of the active agents of the compositions even as the composition translocates over the animal.

Although many solvent systems are available, a skilled formulator cannot predict which system will effectively work for a given combination of active ingredients. However, the presently described solvent system solves the problems of formulating fipronil and permethrin together in effective amounts that result in surprising enhanced repellency against certain parasitic flies, including stable flies, wherein the effective concentrations of fipronil and permethrin resulting in the enhanced repellency are maintained.

Fipronil (5-amino-3-cyano-1-(2,6-dichloro-4-trifluoromethylphenyl)-4-trifluoromethylsulfinylpyrazole) is a 1-N-arylpyrazole insecticide. It has the following structure:

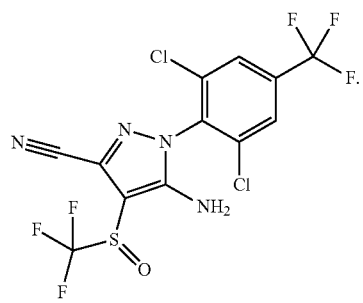 [SMILES: N#Cc1nn(-c2c(Cl)cc(C(F)(F)F)cc2Cl)c(N)c1S(=O)C(F)(F)F]

It is a member of a class of chemicals that are well known in the art, as well as methods for their use in controlling parasites including insect pests, such as fleas, stable flies, horn flies, or mosquitoes, and acarid pests, such as ticks, mites, and lice, in mammals, such as domesticated livestock or companion animals or birds, either alone or in combination with other pesticides such as insect growth regulators. See, e.g., EP-A-295,217, EP 295 177, EP-A-840-686, EP-A-352,944, WO 00/35844, WO 98/39972, U.S. Pat. No. 5,122, 530 5,236,938, 5,232,940, 5,576,429 5,814,652, 5,567,429, 6,090,751 and 6,096,329. These references are hereby incorporated herein in their entirety. The compounds of the families defined in these patents are extremely active. Fipronil is particularly effective, but not exclusively effective, against fleas and ticks. However, fipronil is not known to have any repellent activity against ectoparasites.

Permethrin is a member of the pyrethroids. It has the following structure:

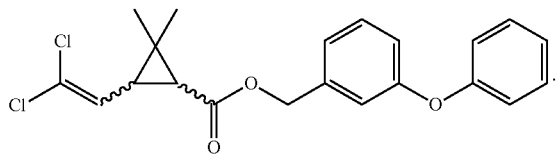 [SMILES: CC1(C)C(C=C(Cl)Cl)C1C(=O)OCc1cccc(Oc2ccccc2)c1]

The pyrethroids are a class of synthetically derived insecticides. These compounds are particularly effective against the mosquito (*Culex* spp.) that transmits West Nile virus. Pyrethroids are structurally related to naturally occurring pyrethrins, pyrethrin I and pyrethrin II. Synthetic pyrethroids include permethrin (U.S. Pat. No. 4,113,968), resmethrin, and sumithrin (U.S. Pat. Nos. 3,934,023 and 2,348,930). Permethrin is well known for its repellent efficacy against various arthropods. These references are hereby incorporated herein in their entirety.

Combinations of fipronil and pyrethroids, such as permethrin, are known (in particular, EPA Registration submission materials available from a PDMS, searchable database; submitter name: Virbac AH, Inc.) The product sold by the trade name EFFITIX® was approved in the U.S. on Nov. 18, 2011. A material safety data sheet (MSDS) of the product indicates that it contains fipronil, permethrin and diethyleneglycol monoethyl ether. WO 2001/065941 A1 and EP 1013170 A1 propose the combination of an N-arylpyrazole and a pyrethroid in applications against plant pests. JP 11049618 A2 uses similar mixtures to prevent feeding damage on timber constructions. WO 95/22902 A1 uses such mixtures for the direct control of termites. GB2396557 A1 teaches that the treatment of ectoparasites with mixtures of N-arylpyrazoles and pyrethroids (if appropriate also with addition of synergists, such as MGK264 or piperonyl butoxide) is possible when concentrated powder formulations are used. All of these references are hereby incorporated herein in their entirety.

However, in order for the actives to function, it is critical to employ a solvent system that provides the necessary solubility and chemical and physical stability to ensure that effective concentrations responsible for the enhanced repellent efficacy remain in solution after administration and up until the actives cover the animal effectively or reach a locus of infestation. There has been no report of the formulation components required to successfully formulate fipronil and permethrin in combination where permethrin is present at high concentrations in a spot-on or pour-on formulation that maintains concentrations under a variety of conditions that result in enhanced repellency against certain ectoparasites including, but not limited to, stable flies. Even skilled formulators cannot predict with reasonable certainty which combinations and solvents will ultimately work together.

In an embodiment, the present subject matter is directed to a formulation comprising permethrin in a concentration of from about 30% w/w to about 55% w/w; fipronil in a concentration of from about 2% w/w to about 15% w/w; and a) one or more neutral oils and b) N-methyl pyrrolidone (NMP).

In another embodiment, the invention provides a formulation comprising permethrin in a concentration of from about 30% w/w to about 55% w/w; fipronil in a concentration of from about 2% w/w to about 15% w/w; and a) one or more neutral oils and b) NMP, wherein the a) one or more neutral oils and b) NMP are present in a weight:weight ratio of from about 1:18 to about 1:2.8, neutral oil(s) to NMP. In this embodiment, if an antioxidant is present, it may be present in a concentration of not more than about 0.25% (w/w).

In still another embodiment, the invention provides a formulation comprising permethrin in a concentration of from about 30% w/w to about 55% w/w; fipronil in a concentration of from about 2% w/w to about 15% w/w; and a) one or more neutral oils and b) NMP, wherein the a) one or more neutral oils and b) NMP are present in a weight: weight ratio of from about 1:2.0 to about 1:3.5, neutral oil(s) to NMP. In this embodiment, if an antioxidant is present, it may be present in a concentration of not more than about 0.25% (w/w).

In one embodiment, the invention provides a formulation comprising permethrin in a concentration of at least about 40% w/w; fipronil in a concentration of at least about 5% w/w; and a) one or more neutral oils and b) NMP, wherein the a) one or more neutral oils and b) NMP are present in a weight:weight ratio of from about 1:1.18 to about 1:2.8 or about 1:2.0 to about 1:3.5, neutral oil(s) to NMP. In this embodiment, if an antioxidant is present, it may be present in a concentration of not more than about 0.25% (w/w).

In another embodiment, the invention provides a formulation comprising permethrin in a concentration of at least about 40% w/w; fipronil in a concentration of at least about 5% w/w; and a) one or more neutral oils and b) NMP, wherein the a) one or more neutral oils and b) NMP are present in a ratio of from about 1:2.5 to about 1:3.5, neutral oil(s) to NMP. In this embodiment, if an antioxidant is present, it may be present in a concentration of not more than about 0.25% (w/w).

In still another embodiment, the invention provides a formulation comprising permethrin in a concentration of from about 40% w/w to about 55% w/w; fipronil in a concentration of from about 5% w/w to about 15% w/w; and a) one or more neutral oils and b) NMP, wherein the a) one or more neutral oils and b) NMP are present in a weight: weight ratio of from about 1:1.8 to about 1:2.8 or about 1:2.0 to about 1:3.5, neutral oil(s) to NMP. In this embodiment, if an antioxidant is present, it may be present in a concentration of not more than about 0.25% (w/w).

In still another embodiment, the invention provides a formulation comprising permethrin in a concentration of from about 40% w/w to about 55% w/w; fipronil in a concentration of from about 5% w/w to about 15% w/w; and a) one or more neutral oils and b) NMP, wherein the a) one or more neutral oils and b) NMP are present in a ratio of from about 1:2.5 to about 1:3.5, neutral oil(s) to NMP. In this embodiment, if an antioxidant is present, it may be present in a concentration of not more than about 0.25% (w/w).

In yet another embodiment, the invention provides a formulation comprising permethrin in a concentration of from about 40% w/w to about 50% w/w; fipronil in a concentration of from about 5% w/w to about 10% w/w; and a) one or more neutral oils and b) NMP, wherein the a) one or more neutral oils and b) NMP are present in a ratio of from about 1:2.5 to about 1:3.0, neutral oil(s) to NMP. In this embodiment, if an antioxidant is present, it may be present in a concentration of not more than about 0.25% (w/w).

In one embodiment of the invention, the level of fipronil sulfone in the compositions described herein is below about 6% by area relative to the area of the fipronil peak measured by high pressure liquid chromatography (HPLC) at about three months after formulation. In other embodiments fipronil sulfone levels will be below about 5% at about three months after formulation or below about 4% at about three months after formulation. In still other embodiments fipronil sulfone levels will be below about 3.5% at about three months after the formulation is prepared. In another embodiment, the fipronil sulfone level will be below about 3.2% at about three months formulation, below about 3.1% at about three months formulation, below about 3.0% at about three months formulation, below about 2.9% at about three months after formulation or below about 2.8% at about three months formulation. In other embodiments, fipronil sulfone levels will be below about 2.7% at about three months after formulation, below about 2.6% at about three months formulation, or below about 2.5% at about three months after formulation. In yet other embodiments, fipronil sulfone levels will be below about 2.4% at about three months after formulation, below about 2.3% at about three months after formulation, below about 2.2% at about three months after formulation. In yet another embodiment, fipronil sulfone levels will be below about 2.1% at about three months after formulation or below about 2.0% at about three months formulation. As used herein, "about three months after formulation" means a period of from 10 weeks to 14 weeks from the time that the fipronil is contacted with other components in the formulation. Typically, it is the time from contact of the fipronil with NMP. The fipronil sulfone level is determined by HPLC relative to the area of the fipronil peak in the sample.

It is the ratio of one or more neutral oils to NMP that provides unique stability of the two active ingredients, permethrin and fipronil in the present formulations, particularly since the neutral oil(s) will be selected so as to not introduce significant amounts of peroxide species. Unlike distinct formulations known in the art for different actives, the formulations disclosed herein are capable of solubilizing permethrin and inhibiting or preventing its crystallization, while also limiting the formation of fipronil sulfone in solution. Consequently, both active ingredients are available in the desired concentrations, which are shown herein to have unexpected enhanced efficacy against stable flies.

A useful concentration of fipronil in the compositions is from about 2% (w/w) to about 15% (w/w). In one embodiment, fipronil is present in a concentration of from about 3% (w/w) to about 10% (w/w). In another embodiment, fipronil is present in a concentration of from about 4% (w/w) to about 8% (w/w). In yet another embodiment fipronil is present at a concentration of about 6% (w/w).

A useful concentration of permethrin in the compositions of the invention is from about 35% (w/w) to about 50% (w/w). In one embodiment, permethrin is present at a concentration of from about 40% (w/w) to about 48% (w/w). In another embodiment, permethrin is present in a concentration of about 42% (w/w) to about 47% (w/w). In still another embodiment, permethrin is present at a concentration of about 45% (w/w).

In some embodiments, the invention provides the following formulations: Formulation A) fipronil about 6% (w/w); permethrin about 45% (w/w); NMP about 35% (w/w); DGME (diethyleneglycol monoethyl ether or TRANSCUTOL®) in an amount sufficient to complete the formulation (QS or quantum sufficit) about 10-15% (w/w) and about 0.1% (w/w) BHT; Formulation B) fipronil about 6% (w/w); permethrin about 45% (w/w); NMP about 35% (w/w); MIGLYOL® 812 in an amount sufficient to complete the formulation (QS) about 10-15% (w/w) and about 0.1% (w/w) BHT. In some embodiments, the amount of DGME in Formulation A) will be about 12-14%, about 12% (w/w), about 13% (w/w) or about 14% (w/w). In other embodiments, the amount of MIGLYOL® in Formulation B) will be about 12% (w/w), about 13% (w/w) or about 14% (w/w).

Dosages of the actives can be readily determined by those of skill in the art. However, in general terms, a dose of from about 0.001 to about 100 mg per kg of body weight, more typically from about 0.01 mg to about 50 mg/kg of body weight, given as a single dose or in divided doses for a period of from 1 to 5 days may be satisfactory but, of course, there can be instance where higher or lower dosage ranges are indicated and such are within the scope of this specific administration period for a particular situation. It will be understood that the dosing volume of a formulation can also be determined and then adjusted as desired.

In some embodiments, the composition comprises fipronil at about 6.0% (w/w) and permethrin at about 45 (w/w). This composition also comprises the N-methyl pyrrolidone and neutral oil solvent system described herein.

The neutral oil(s) and N-methyl pyrrolidone components can be quantified in terms of the relative amounts of each. In some embodiments, useful weight:weight ratios of neutral oil(s) to NMP are from 1:1.8 to about 1:3.5; or about 1:2.0 to about 1:3.5. In other embodiments, ratios include from about 1:1.9 to about 1:2.7; about 1:2.0 to about 1:3.0; and about 1:2.5 to about 1:3.0, neutral oil(s) to NMP. In other embodiments ratio values include: 1:1.9, 1:2, 1:2.1, 1:2.2, 1:2.4, 1:2.5, 1:2.6, 1:2.7, 1:2.8, 1:2.9, 1:3.0, 1:3.1, 1:3.2, 1:3.3, 1:3.4 and 1:3.5, neutral oil(s) to NMP. In yet other embodiments, ratios include from about 1:2.2 to about 1:2.4, neutral oil(s) to NMP. In another embodiment, the ratio is about 1:2.3 to about 1:3.0, neutral oil(s) to NMP. These ratios are relative amounts, but are suitably based on a useful amount of neutral oil(s) or NMP.

Useful concentrations of NMP in the compositions are from about 25% (w/w) to about 44% (w/w). In one embodiment, the concentration of NMP is from about 28% (w/w) to about 42% (w/w) or from about 31% (w/w) to about 39% (w/w). In still other embodiments, the concentration of NMP is from 33% (w/w) to about 37% (w/w). In yet another embodiment, NMP is present at a concentration of about 35% (w/w). From the level of NMP present or intended, a corresponding amount of diluent can be calculated.

The compositions contain an amount of neutral oil that minimizes fipronil sulfone formation in the formulation comprising fipronil and NMP. The amount of the neutral oil used in the formulations may vary slightly as it is used in an amount to complete the formulation (QS). Useful concentrations of neutral oil(s) in the compositions of the invention include, but are not limited to, about 11% (w/w) to about 18% (w/w). In some embodiments, concentrations of neutral oil(s) include from about 12% (w/w) to about 17% (w/w) and from about 13% (w/w) to about 16% (w/w). In other embodiments, the neutral oil(s) are present in a concentration of from about 12% (w/w) to about 14% (w/w), about 13% (w/w) to about 15% (w/w). In another embodiment, the neutral oil is present at a concentration of about 14% (w/w).

When present in preferred embodiments, an antioxidant is beneficially present at a concentration of not more than about 0.25% (w/w), although higher concentrations could be added. In some embodiments, the concentration is not more than about: 0.2% (w/w); 0.19% (w/w); 0.18% (w/w); 0.17% (w/w); 0.16% (w/w); 0.15% (w/w); 0.14% (w/w); 0.13% (w/w); 0.12% (w/w) or 0.11% (w/w). In another embodiment, if present, the antioxidant is present at a concentration of not more than about 0.1% (w/w). Suitable inorganic antioxidants are, for example, the sulphites and bisulphites, in particular sodium bisulphite. In one embodiment, the antioxidant is a phenolic antioxidant, such as anisole, butylated hydroxytoluene and butylated hydroxyanisole, and their mixtures with one another. In other embodiments, the antioxidizing agents are those conventional in the art and include, for example, ascorbic acid, sodium metabisulphite, propyl gallate, sodium thiosulphate or a mixture of not more than two of them. When used in formulations containing NMP and a diluent that does not significantly add peroxide species to the formulation, the amount of antioxidant can be beneficially kept substantially below the amount required in formulations that do not contain the beneficial solvent systems of the invention.

In other embodiments, the present subject matter is directed to a pesticidal composition that exhibits surprising and unexpected repellency against parasites, including stable flies, comprising from about 2% (w/w) to about 15% (w/w) fipronil; from about 30% (w/w) to about 55% (w/w) permethrin; a glycol, glycol ether, glycol ester or fatty acid ester and N-methyl pyrrolidone, wherein said glycol, glycol ether, glycol ester, or fatty acid ester and N-methyl pyrrolidone are present in a weight:weight ratio of about 1:1.8 to about 1:2.8, about 1:2.0 to about 1:3.5, about 1:2.0 to about 1:3.0, about 1:2.5 to about 1:3.5, or about 1:2.5 to about 1:3.0; and optionally an antioxidant.

In another embodiment, the present subject matter is directed to a pesticidal composition comprising at least about 5% (w/w) fipronil; at least about 40% (w/w) permethrin; a glycol, glycol ether, glycol ester or fatty acid ester and N-methyl pyrrolidone, wherein said glycol, glycol ether, glycol ester or fatty acid ester and N-methyl pyrrolidone are present in a weight:weight ratio of about 1:2.0 to about 1:3.5, about 1:2.0 to about 1:3.0, about 1:2.5 to about 1:3.5, or about 1:2.5 to about 1:3.0; and optionally an antioxidant, wherein the composition provides unexpected enhanced repellency against parasitic flies, including stable flies.

In another embodiment, the present subject matter is directed to a pesticidal composition comprising about 5% (w/w) to about 15% (w/w) fipronil; about 40% (w/w) to about 55% (w/w) permethrin; a glycol, glycol ether, glycol ester or fatty acid ester and N-methyl pyrrolidone, wherein said glycol, glycol ether, glycol ester or fatty acid ester and N-methyl pyrrolidone are present in a ratio of about 1:2.0 to about 1:3.5; and optionally an antioxidant.

In another embodiment, the present subject matter is directed to a pesticidal composition comprising about 5% (w/w) to about 10% (w/w) fipronil; about 40% (w/w) to about 50% (w/w) permethrin; a glycol, glycol ether, glycol ester or fatty acid ester and N-methyl pyrrolidone, wherein said glycol, glycol ether, glycol ester or fatty acid ester and N-methyl pyrrolidone are present in a ratio of about 1:2.0 to about 1:3.5; and optionally an antioxidant.

In another embodiment, the present subject matter is directed to a pesticidal composition comprising about 6% (w/w) (w/w) fipronil; about 45% (w/w) permethrin; a glycol, glycol ether, glycol ester or fatty acid ester and N-methyl pyrrolidone, wherein said glycol, glycol ether, glycol ester or fatty acid ester and N-methyl pyrrolidone are present in a ratio of about 1:2.0 to about 1:3.5; and optionally an antioxidant.

Useful amounts of permethrin and fipronil in these formulations are as described above. In some embodiments, the formulations described above provide unexpected enhanced repellency against parasitic flies, including stable flies, and superior insecticidal efficacy.

In these embodiments, the antioxidant may be present at concentrations of from about 0.005 to about 1% (w/w) or from about 0.01 to about 0.05% (w/w). In some embodiments, the antioxidant may be present in a concentration of about 0.01 to about 1% by weight, or from about 0.05% to about 0.5% by weight. In another embodiment, the antioxidant is present in a concentration of from about 0.075 to about 0.2% by weight. Amounts lower than 0.2% by weight are useful depending on the peroxide levels in the diluent that is selected or the NMP.

Glycols useful in the compositions include of diethylene glycol, polyethylene glycol (PEG, including all low molecular weight to high molecular weight PEG), propylene glycol and polypropylene glycol. Glycol ethers include, but are not limited to, methyl diglycol, ethyl diglycol, propyl diglycol, butyl diglycol, methyl glycol, ethyl glycol, ethylene glycol monomethyl ether, diethylene glycol monomethyl ether, diethylene glycol monoethyl ether, propylene glycol monomethyl ether and tetrahydrofurfuryl alcohol polyethylene glycol ether (tetraglycol or glycofurol). In one embodiment, the glycol ether is diethylene glycol monoethyl ether. Glycol esters that may be used in the formulations include carboxylic acid esters of glycols or glycol ethers including, but are not limited to, acetates of glycols and glycol ethers such as ethylene glycol monoethyl ether acetate (ethyl CELLOSOLVE™ acetate), ethyleneglycol monobutyl ether acetate (butyl CELLOSOLVE™ acetate), ethyleneglycol monomethyl ether acetate, and the like.

In the embodiment described above comprising a glycol, glycol ether, glycol ester or fatty acid ester and NMP, concentrations of NMP in the compositions of the invention may be from about 25% (w/w) to about 44% (w/w). In other embodiments, NMP may be present in a concentration of about 28% (w/w) to about 42% (w/w) or from about 31% (w/w) to about 39% (w/w). In still other embodiments, NMP may be present at a concentration of about 33% (w/w) to about 37% (w/w). In another embodiment, NMP may be present at a concentration of about 35% (w/w). From the level of NMP present or intended, a corresponding amount of diluent can be calculated.

The glycol, glycol ether, glycol ester or fatty acid ester and N-methyl pyrrolidone components can be quantified in terms of the relative amounts of each. Useful weight:weight ratios of glycol, glycol ether, glycol ester or fatty acid ester to NMP include a ratio of from 1:2.0 to about 1:3.5. In other embodiments, the ratios include from about 1:1.18 to about 1:1.28, about 1:2.0 to about 1:3.0; about 1:1.9 to about 1:2.7; about 1:2.0 to about 1:2.6; and about 1:2.5 to about 1:3.0, glycol, glycol ether or fatty acid ester to NMP. In still other embodiments, the weight:weight ratio of glycol, glycol ether or fatty acid ester to NMP will be 1:1.9, 1:2, 1:2.1, 1:2.2, 1:2.4, 1:2.5, 1:2.6, 1:2.7, 1:2.8, 1:2.9, 1:3.0, 1:3.1, 1:3.2, 1:3.3, 1:3.4 or 1:3.5. In other embodiments of the invention, the weight:weight ratio of glycol, glycol ether, glycol ester or fatty acid ester to NMP will be from about 1:2.5 to about 1:3.0 or about 1:2.5 to about 1:3.5. These ratios are relative amounts, but are suitably based on a useful amount of glycol, glycol ether or fatty acid ester, or NMP.

In certain embodiments, the compositions contain an amount of glycol, glycol ether, glycol ester or fatty acid ester that minimizes fipronil sulfone formation in the formulation comprising fipronil and NMP. Typically, the amount of glycol, glycol ether, glycol ester or fatty acid ester used in the formulations will an amount sufficient to complete the formulation (QS) and will thus vary slightly. Useful concentrations of glycol, glycol ether, glycol ester or fatty acid ester include from about 11% (w/w) to about 18% (w/w). In other embodiments, the concentration of a glycol, glycol ether, glycol ester or fatty acid ester are from about 12% (w/w) to about 17% (w/w) or from about 13% (w/w) to about 16% (w/w). In yet other embodiments of the invention, the concentration of the glycol, glycol ether or fatty acid ester are from about 12% (w/w) to about 14% (w/w) or from about 13% (w/w) to about 15% (w/w). In another embodiment, the glycol, glycol ether or fatty acid ester is present at a concentration of about 14% (w/w).

In all embodiments, other solvents and/or diluents may be used in the formulations of the invention. In one embodiment, long-chain alkyl amides may also be used so long as they provide the necessary solubility and physical and chemical stability to maintain the desired concentrations of fipronil and permethrin before and after application. These include systems which employ glycerol formal, decanamides and octanamides, such as N,N-dimethyldecanamide (DMDA). Glycerol formal is a mixture of 5-hydroxy-1,3-dioxane and 4-hydroxymethyl-1,3-dioxolane (60:40). In one embodiment, the glycerol formal that is added to a formulation of the invention is stabilized glycerol formal. Stabilized glycerol formal typically contains 0.02% disodium EDTA, 0.02% N-propyl gallate, and 0.01% thiopropionic acid. However, in certain embodiments for topical applications, the compositions will include neutral oils as the diluent.

Additional Active Agents

In one embodiment, the invention provides topical compositions comprising fipronil and permethrin in combination with one or more additional active agents. In some embodiments, the additional active agents combined with fipronil and permethrin may include, but are not limited to, acaricides, anthelmintics, insecticides and other parasiticides of various classes presented herein.

In another embodiment, the topical compositions may also include veterinary therapeutic agents. Veterinary pharmaceutical agents that may be included in the compositions of the invention are well-known in the art (see e.g. *Plumb' Veterinary Drug Handbook*, 5$^{th}$ Edition, ed. Donald C. Plumb, Blackwell Publishing, (2005) or *The Merck Veteri-*

*nary Manual*, 9*th* Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, additional arylpyrazole compounds such as phenylpyrazoles may be included in the topical compositions of the invention. The arylpyrazoles are known in the art and are suitable for combination with the isoxazoline compounds in the soft chewable compositions of the invention. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference).

In another embodiment of the invention, one or more macrocyclic lactones or lactams, which act as an acaricide, an anthelmintic agent and/or an insecticide, can be included in the compositions of the invention. For the avoidance of doubt, the term "macrocyclic lactone" as used herein includes both naturally occurring and synthetic or semisynthetic avermectin and milbemycin compounds.

The macrocyclic lactones that may be used in the compositions of the invention include, but are not limited to, the naturally produced avermectins (e.g. including the components designated as $A_1a$, $A_1b$, $A_2a$, $A_2b$, $B_1a$, $B_1b$, $B_2a$ and $B_2b$) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054, both incorporated herein by reference.

The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996).

Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054, all incorporated herein by reference.

In one embodiment, the topical compositions of the invention comprise an effective amount of at least one of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin or nemadectin, or a combination thereof. In another embodiment, the topical veterinary compositions of the invention may comprise an effective amount of at least one of abamectin, emamectin, eprinomectin, ivermectin, doramectin or selamectin, or a combination thereof. In still another embodiment, the topical compositions of the invention may comprise an effective amount of at least one of ivermectin, milbemectin, milbemycin oxime or moxidectin, or a combination thereof.

In another embodiment of the invention, the topical composition comprising fipronil and permethrin may include a class of active agents known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the compositions of the invention may include an IGR compound that mimics juvenile hormone or that modulates levels of juvenile hormones in insects. Examples of juvenile hormone mimics include azadirachtin, diofenolan, fenoxycarb, hydroprene, kinoprene, methoprene, pyriproxyfen, tetrahydroazadirachtin and 4-chloro-2 (2-chloro-2-methyl-propyl)-5-(6-iodo-3-pyridylmethoxy) pyridazine-3(2H)-one.

In another embodiment, the compositions of the invention include an IGR compound that is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In some embodiments, the compositions of the invention may include one or more antinematodal agents including, but not limited to, active agents in the benzimidazoles, imidazothiazoles, tetrahydropyrimidines and the organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole.

In still other embodiments, the compositions of the invention may include tetrahydropyrimidine active agents including, but not limited to, pyrantel, oxantel, and morantel.

Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, nitroxynil, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin, paromomycin II, praziquantel and epsiprantel.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a (4H)-dibenzofurancarboxaldehyde (MGK-11), 2-(2-ethylhexyl)-3a,4,7,7a-tetrahydro-4,7-methano-1H-isoindole-1,3 (2H)dione (MGK-264), dipropyl-2,5-pyridinedicarboxylate (MGK-326) and 2-(octylthio)ethanol (MGK-874).

In another embodiment, an antiparasitic agent that can be included in the topical veterinary composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Wilson et al., *Parasitology*, January 2003, 126(Pt 1):79-86).

In another embodiment, the topical compositions of the invention may comprise an active agent from the neonicotinoid class of parasiticides. The neonicotinoids bind and inhibit insect specific nicotinic acetylcholine receptors. In one embodiment, the neonicotinoid insecticidal agent that can be included in the topical compositions of the invention is imidacloprid. Agents of this class are described, for example, in U.S. Pat. No. 4,742,060 or in EP 0 892 060 (both incorporated herein by reference). In another embodiment, the compositions of the invention may comprise nitenpyram, another active agent of the neonicotinoid class of pesticides. The use of nitenpyram for controlling fleas is described in U.S. Pat. No. 5,750,548, which is incorporated herein by reference in its entirety.

In other certain embodiments of the invention, an insecticidal agent that can be combined with the compositions of the invention is a semicarbazone, such as metaflumizone.

In another embodiment, the compositions of the invention may advantageously include one or more other isoxazoline compounds known in the art. These active agents, which are very effective against ectoparasites, are described in U.S. Pat. No. 7,964,204 and WO 2007/079162; US 2010/0254960 A1, US2011/0159107, US2012/0309620, US2012/0030841, US2010/0069247, WO 2007/125984, WO 2012/086462, U.S. Pat. No. 8,318,757, US 2011/0144349, U.S. Pat. No. 8,053,452; US 2010/0137612, US 2010/0254959, US 2011/152081, WO 2012/089623, WO 2012/089622, U.S. Pat. No. 8,119,671; U.S. Pat. No. 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, U.S. Pat. No. 7,897,630, U.S. Pat. No. 7,951,828; WO 2011/075591 and US 2011/0152312, and U.S. Pat. No. 7,662,972, all of which are incorporated herein by reference in their entirety.

In another embodiment of the invention, nodulisporic acid and its derivatives may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in U.S. Pat. No. 7,084,280 to Ducray et al. (incorporated herein by reference); Sager et al., Veterinary Parasitology, 2009, 159, 49-54; Kaminsky et al., Nature vol. 452, 13 Mar. 2008, 176-181.

The compositions of the invention may also include aryloazol-2-yl cyanoethylamino compounds such as those described in U.S. Pat. No. 8,088,801 and US 2010/0125089 to Soll et al., which is incorporated herein by reference, and thioamide derivatives of these compounds, as described in U.S. Pat. No. 7,964,621 to Le Hir de Fallois, which is also incorporated herein by reference.

The compositions of the invention may also include paraherquamide compounds and derivatives of these compounds, including derquantel (see Ostlind et al., *Research in Veterinary Science*, 1990, 48, 260-61; and Ostlind et al.,

*Medical and Veterinary Entomology,* 1997, 11, 407-408). The paraherquamide family of compounds is a known class of compounds that include a spirodioxepino indole core with activity against certain parasites (see *Tett. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.-Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432 and US 2010/0197624, U.S. Pat. No. 5,703,078 and U.S. Pat. No. 5,750,695, all of which are hereby incorporated by reference in their entirety.

In another embodiment of the invention, the compositions may include a spinosyn active agent produced by the soil actinomycete *Saccharopolyspora spinosa* (see, for example Salgado V. L. and Sparks T. C., "*The Spinosyns: Chemistry, Biochemistry, Mode of Action, and Resistance,*" in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona,* which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, the additional active agent is included in the dosage units of the invention in an amount of between about 0.1 µg and about 1000 mg. Typically, the active agent may be included in an amount of about 10 µg to about 500 mg, about 10 µg to about 400 mg, about 1 mg to about 300 mg, about 10 mg to about 200 mg or about 10 mg to about 100 mg. More typically the active agent will be present in an amount of about 5 mg to about 50 mg in the compositions of the invention.

The concentration of the additional active agent(s) in the topical compositions of the invention will typically be from about 0.01% to about 30% (w/w) depending on the potency of the active agent. In certain embodiments for very potent active agents including, but not limited to a macrocyclic lactone active agent, the concentration of the active agent will typically be from about 0.01% to about 10% (w/w), from about 0.01 to about 1% (w/w), from about 0.01% to about 0.5% (w/w), from about 0.1% to about 0.5% (w/w) or from about 0.01% to about 0.1% (w/w). In other embodiments, the concentration of the active agent will typically be from about 0.1% to about 2% (w/w) or about 0.1% to about 1% (w/w).

In other embodiments, the additional active agent(s) will typically be present at higher concentrations to achieve the desired efficacy. In some embodiments, the active agent will be present in a concentration of about 1% to about 30% (w/w), about 1% to about 20% (w/w) or about 1% to about 15% (w/w). In still other embodiments, the active agent will be present in a concentration of about 5% to about 20% (w/w) or about 5% to about 15% (w/w) in the composition.

In various embodiments of the invention, an additional active agent may be included in the composition to deliver a dose of about 0.001 mg/kg to about 50 mg/kg or about 0.5 mg/kg to about 50 mg/kg of body weight of the animal. In other embodiments, the active agent will typically be present in an amount sufficient to deliver a dose of about 0.05 mg/kg to about 30 mg/kg, about 0.1 mg/kg to about 20 mg/kg. In other embodiments, the active agent will be present in an amount sufficient to deliver a dose of about 0.1 mg/kg to about 10 mg/kg, about 0.1 mg/kg to about 1 mg/kg or about 0.5 mg/kg to about 50 mg/kg per body weight of the animal.

In certain embodiments of the invention where the additional active agent is a very potent compound such as a macrocyclic lactone or other potent compounds, the active agent will be present in a concentration to provide a dose of about 0.001 mg/kg to about 5 mg/kg, about 0.001 mg/kg to about 0.1 mg/kg or about 0.001 mg/kg to about 0.01 mg/kg. In still other embodiments, the active agent is present in an amount sufficient to deliver a dose of about 0.01 mg/kg to about 2 mg/kg or about 0.1 mg/kg to about 1 mg/kg per body weight of the animal. In still other embodiments, the additional active agent may be present in an amount to deliver a dose of about 1 µg/kg to about 200 µg/kg or about 0.1 mg/kg to about 1 mg/kg of weight of animal.

Methods and Uses

In an embodiment, the present subject matter is directed to a method of treating and/or controlling a parasite infestation in an animal. The method comprises administering an effective amount of a formulation described herein to the animal. Surprisingly, it has been found and disclosed herein that at particular concentrations, fipronil and permethrin have surprisingly enhanced repellent activity against stable fly. In one embodiment, the formulations of the invention having a combination of fipronil and permethrin were unexpectedly found to have a significantly higher repellent efficacy against stable flies compared to a formulation containing permethrin alone at the same concentration administered to deliver the same dose. The observed enhanced repellent efficacy is surprising because fipronil, although a very potent insecticidal agent, is not known to have repellent efficacy against ectoparasites. Accordingly, one method of the invention is directed to combating pest infestations of parasitic flies including stable fly (*Stomoxys calcitrans*) and horn fly (*Haematobia irritans*), among other fly species.

In other embodiments, the uses and methods of the invention are for treating and/or preventing parasite infestations and/or infections from pests including those from the order of the Anoplura, for example, *Haematopinus* spp., *Linognathus* spp., *Solenopotes* spp., *Pediculus* spp., *Pthirus* spp.; from the order of the Mallophaga, for example, *Trimenopon* spp., *Menopon* spp., *Eomenacanthus* spp., *Menacanthus* spp., *Trichodectes* spp., *Felicola* spp., *Damalinea* spp., *Bovicola* spp.; from the order of the Diptera, suborder Brachycera, for example, *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cordylobia* spp., *Cochliomyia* spp., *Chrysomyia* spp., *Sarcophaga* spp., *Wohlfahrtia* spp., *Gasterophilus* spp., *Oedemagena* spp., *Hypoderma* spp., *Oestrus* spp., *Rhi-*

*noestrus* spp., *Melophagus* spp., *Hippobosca* spp.; from the order of the Diptera, suborder Nematocera, for example, *Culex* spp., *Aedes* spp., *Anopheles* spp., *Culicoides* spp., *Phlebotomus* spp., *Simulium* spp.; from the order of the Siphonaptera, for example, *Ctenocephalides* spp., *Echidnophaga* spp., *Ceratophyllus* spp., *Pulex* spp.; from the order of the Metastigmata, for example, *Hyalomma* spp., *Rhipicephalus* spp., *Boophilus* spp., *Amblyomma* spp., *Haemaphysalis* spp., *Dermacentor* spp., *Ixodes* spp., *Argas* spp., *Otobius* spp.; from the order of the Mesostigmata, for example, *Dermanyssus* spp., *Ornithonyssus* spp., *Pneumonyssus* spp.; from the order of the Prostigmata, for example, *Cheyletiella* spp., *Psorergates* spp., *Myobia* spp., *Demodex* spp., *Neotrombicula* spp.; from the order of the Astigmata, for example, *Acarus* spp., *Myocoptes* spp., *Psoroptes* spp., *Chorioptes* spp., *Otodectes* spp., *Sarcoptes* spp., *Notoedres* spp., *Knemidocoptes* spp., *Neoknemidocoptes* spp., *Cytodites* spp., *Laminosioptes* spp.; and fleas (Siphonaptera, for example, *Ctenocephalides* spp., *Echidnophaga* spp., *Ceratophyllus* spp., *Pulex* spp.), ticks (*Hyalomma* spp., *Rhipicephalus* spp., *Boophilus* spp., *Amblyomma* spp., *Haemaphysalis* spp., *Dermacentor* spp., *Ixodes* spp., *Argas* spp., *Ornithodorus* spp., *Otobius* spp.) and in particular the Diptera mentioned above (*Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cordylobia* spp., *Cochliomyia* spp., *Chrysomyia* spp., *Sarcophaga* spp., *Gasterophilus* spp., *Oedemagena* spp., *Hypoderma* spp., *Oestrus* spp., *Rhinoestrus* spp., *Melophagus* spp., *Hippobosca* spp.).

In another embodiment, the subject matter disclosed herein is directed to a method for cleaning the coats and the skin of animals by removal of the parasites which are present and of their waste and excreta and administering to the animal a formulation as described herein. The animals treated thus exhibit a coat which is more pleasing to the eye and more pleasant to the touch.

The term "animal" as used herein refers to any mammal or bird. In particular, cattle, sheep, horses, pigs, chicken, and dogs would benefit from administration of the compositions disclosed herein as they may be infested by parasites that are effectively controlled by the compositions. The useful and breeding animals include mammals, such as, for example, cattle, horses, zebras, sheep, pigs, goats, camels, yaks, water buffalo, donkeys, fallow deer, reindeer, rodents, fur-bearing animals, such as, for example, mink, chinchilla, raccoon, birds, such as, for example, hens, chickens, geese, turkeys, quails and ducks. Domesticated animals include dogs, and particular emphasis is given to the treatment of dogs.

Various methods of formulating parasiticidal formulations are known in the art. These include oral formulations, dietary supplements, powders, skin solutions (pour-on or spot-on), sprays, drenches, baths, showers, jets, powders, greases, shampoos and creams.

Of particular interest are formulations for localized topical applications of parasiticidal active agents known in the art as spot-on or pour-on formulations. Each type of formulation has distinct properties. For example, pour-on solutions comprising 1-N-phenylpyrazole derivatives, such as fipronil, are known in the art and are described in, for example, U.S. Pat. No. 6,010,710, U.S. Pat. No. 6,413,542, U.S. Pat. No. 6,001,384 and U.S. Pat. No. 6,413,542. Spot-on formulations are well known techniques for topically delivering certain antiparasitic agents with the required physicochemical properties to a limited area of the host. For example, U.S. Pat. No. 5,045,536 describes such formulations for ectoparasites. Other spot-on formulations include U.S. Pat. No. 6,426,333 and U.S. Pat. No. 6,482,425. All of these references are hereby incorporated herein in their entirety.

In one embodiment, the composition is a spot-on formulation comprising from about 2% (w/w) to about 10% (w/w) fipronil; from about 30% (w/w) to about 55% (w/w) permethrin; and a glycol, glycol ether, glycol ester, fatty acid ester or neutral oil and N-methyl pyrrolidone, wherein said glycol, glycol ether, glycol ester, fatty acid ester or neutral oil and N-methyl pyrrolidone are present in a ratio of from about 1:1.8 to about 1:2.8 or about 1:2.0 to about 1:3.5, glycol, glycol ether, glycol ester, fatty acid ester or neutral oil to NMP, and further wherein said composition is a liquid having a volume of from about 0.5 mL to about 10 mL. In another embodiment, the volume of the spot-on composition is from about 1 mL to about 6 mL.

In another embodiment, the composition is a spot-on formulation comprising at least about 5% (w/w) fipronil; at least about 40% (w/w) permethrin; and a glycol, glycol ether, glycol ester, fatty acid ester or neutral oil and N-methyl pyrrolidone, wherein said glycol, glycol ether, glycol ester, fatty acid ester or neutral oil and N-methyl pyrrolidone are present in a weight:weight ratio of from about 1:1.8 to about 1:2.8 or about 1:2.0 to about 1:3.5, glycol, glycol ether, glycol ester, fatty acid ester or neutral oil to NMP, and further wherein said composition is a liquid having a volume of from about 0.5 mL to about 10 mL. In another embodiment, the volume of the spot-on composition is from about 1 mL to about 6 mL.

In one embodiment, the composition is a spot-on formulation comprising at least about 5% (w/w) fipronil; at least about 40% (w/w) permethrin; and a glycol, glycol ether, glycol ester, fatty acid ester or neutral oil and N-methyl pyrrolidone, wherein said glycol, glycol ether, glycol ester, fatty acid ester or neutral oil and N-methyl pyrrolidone are present in a weight:weight ratio of from about 1:2.5 to about 1:3.5 or about 1:25 to about 1:3.0, glycol, glycol ether, glycol ester, fatty acid ester or neutral oil to NMP, and further wherein said composition is a liquid having a volume of from about 0.5 mL to about 10 mL. In another embodiment, the volume of the spot-on composition is from about 1 mL to about 6 mL.

In still another embodiment, the composition is a spot-on formulation comprising about 5% (w/w) to about 15% (w/w) fipronil; about 40% (w/w) to about 55% (w/w) permethrin; and a glycol, glycol ether, glycol ester, fatty acid ester or neutral oil and N-methyl pyrrolidone, wherein said glycol, glycol ether, glycol ester, fatty acid ester or neutral oil and N-methyl pyrrolidone are present in a weight:weight ratio of from about 1:1.8 to about 1:2.8 or about 1:2.0 to about 1:3.5, glycol, glycol ether, glycol ester, fatty acid ester or neutral oil to NMP, and further wherein said composition is a liquid having a volume of from about 0.5 mL to about 10 mL. In another embodiment, the volume of the spot-on composition is from about 1 mL to about 6 mL.

In still another embodiment, the composition is a spot-on formulation comprising about 5% (w/w) to about 15% (w/w) fipronil; about 40% (w/w) to about 55% (w/w) permethrin; and a glycol, glycol ether, glycol ester, fatty acid ester or neutral oil and N-methyl pyrrolidone, wherein said glycol, glycol ether, glycol ester, fatty acid ester or neutral oil and N-methyl pyrrolidone are present in a weight:weight ratio of from about 1:2.5 to about 1:3.0 or about 1:2.5 to about 1:3.5, glycol, glycol ether, glycol ester, fatty acid ester or neutral oil to NMP, and further wherein said composition is a liquid having a volume of from about 0.5 mL to about 10 mL. In another embodiment, the volume of the spot-on composition is from about 1 mL to about 6 mL.

In another embodiment, the composition is a spot-on formulation comprising about 5% (w/w) to about 10% (w/w) fipronil; about 40% (w/w) to about 50% (w/w) permethrin; and a glycol, glycol ether, glycol ester, fatty acid ester or neutral oil and N-methyl pyrrolidone, wherein said glycol, glycol ether, glycol ester, fatty acid ester or neutral oil and N-methyl pyrrolidone are present in a weight:weight ratio of from about 1:1.8 to about 1:2.8 or about 1:2.0 to about 1:3.5, glycol, glycol ether, glycol ester, fatty acid ester or neutral oil to NMP, and further wherein said composition is a liquid having a volume of from about 0.5 mL to about 10 mL. In another embodiment, the volume of the spot-on composition is from about 1 mL to about 6 mL.

In another embodiment, the composition is a spot-on formulation comprising about 5% (w/w) to about 10% (w/w) fipronil; about 40% (w/w) to about 50% (w/w) permethrin; and a glycol, glycol ether, glycol ester, fatty acid ester or neutral oil and N-methyl pyrrolidone, wherein said glycol, glycol ether, glycol ester, fatty acid ester or neutral oil and N-methyl pyrrolidone are present in a weight:weight ratio of from about 1:2.5 to about 1:3.5 or about 1:2.5 to about 1:3.0, glycol, glycol ether, glycol ester, fatty acid ester or neutral oil to NMP, and further wherein said composition is a liquid having a volume of from about 0.5 mL to about 10 mL. In another embodiment, the volume of the spot-on composition is from about 1 mL to about 6 mL.

The topical composition of the invention can be administered in several ways. Administering comprises contacting the coat and/or skin of said animal with said composition. In one embodiment, the formulation is a spot-on or pour-on formulation. These formulations are applied to the animal's back, along the line of the back for a pour-on formulation or at one or two spots on the back for a spot-on product. In one embodiment, the formulation will be administered to the animal over a highly localized region of the animal, preferably between the shoulder blades. In another embodiment, this localized region has a surface area of less than 10 cm$^2$, especially between 5 and 10 cm$^2$ area. Such contacting or application can take place both prophylactically and therapeutically.

Administration of the formulations may be intermittent in time and may be administered daily, weekly, biweekly, monthly, bimonthly, quarterly, or even for longer durations of time. The time period between treatments depends upon factors such as the target parasite(s), the degree of infestation, the type of mammal or bird being treated and the environment where it resides. It is well within the skill level of the practitioner to determine a specific administration period for a particular situation. The presently described methods are directed to permanently combating a parasite in an environment in which the animal is subjected to strong parasitic pressure where the administration is at a frequency far below a daily administration in this case. For example, in one embodiment the treatment according to the invention will be carried out monthly on mammals such as dogs.

In certain embodiments, the liquid formulations according to the invention are suitable for spray application, where the spray application may be carried out, for example, using a pump spray or an aerosol spray (pressurized spray). For specific indications, the formulations may also be used after dilution with water as a dip; in this case, the formulation should contain emulsifying additives. In one embodiment, the compositions are applied as pour-on and spot-on formulations. The spot-on application is particularly preferred. The formulations according to the invention are distinguished by their excellent compatibility with customary "single-dose" plastic pipettes and by their storage stability in various climate zones. They have low viscosity and can be easily applied.

The liquid formulations according to the invention can be prepared by mixing appropriate amounts of the components with one another, using, for example, conventional stirring tanks or other suitable instruments. If required by the ingredients, it is also possible to operate under a protective atmosphere or with other methods of excluding oxygen. Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

In certain embodiments, compositions described herein do not contain visible solids and are clear, but not necessarily water-clear, solutions having the described synergistic amounts of fipronil and permethrin fully solubilized therein. The two-component solvent system secures the objectives of absence of crystallization on the coat and of maintenance of the cosmetic appearance of the fur, without a tendency towards sticking or towards a sticky appearance, despite the high concentration of actives in the composition.

In some embodiments the formulations disclosed herein can also comprise synergists. Synergists in the sense of this application are to be understood as meaning compounds which for their part do not have the desired activity, but which, as mixing partners, increase the activity of the active compounds. Piperonyl butoxide, MGK264, verbutin, S,S,S-tributyl phosphorotrithioate may be mentioned here in an exemplary manner.

Though not required, the compositions may further include a stability enhancer. A "stability enhancer" is a compound that enhances the stability of an active agent compared to the stability of the active agent in the absence of the stability enhancer. Examples of stability enhancers include glycerol formal and polyethylene glycol (e.g., PEG 200). Other stability enhancers are well-known in this field. In particular embodiments, a small amount of glycerol formal, e.g., 5% or less, can be added. In some embodiments, it may be desirable to add PEG 200 to the formulations of the invention to support the stability enhancement and solvency function of the glycerol formal.

The invention further provides for titration of the amount of stability enhancer that is added to the formulations of the invention. For example, in embodiments where the stability enhancer is glycerol formal, the amount of glycerol formal can be titrated, such that an optimal stability of the fipronil and permethrin composition is achieved in the formulation. The amount of stability enhancer present in a formulation of the invention may be low, such as about 5% w/v or less (e.g., 1.5% w/v). In other embodiments, the stability enhancer will be present in an amount of about 5-25% w/v, such as, for example, 15% w/v.

In some embodiments the solutions according to the invention which are oily, in addition to a glycol ether, may comprise a diluent or vehicle and also a solvent (organic solvent) for the active agent(s). However, due to the ability of the two-component solvent system described herein to solubilize both permethrin and fipronil, the use of addition solubility enhancers would suitably be minimal.

Further, though not required, if desired, crystallization inhibitors can be used in the compositions. These include: polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; sodium abietate; alkyl sulphates, in particular sodium lauryl sulphate and sodium cetyl sulphate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R', R", R'" and R"" radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used, amine salts of formula $N^+HR'R''R'''\ Y^-$, in which the R', R", and R'" radicals are identical or different optionally hydroxylated hydrocarbon radicals and $Y^-$ is as defined above; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, or a mixture of at least two of the compounds listed above.

A crystallization inhibitor pair can be used. Such pairs include, for example, the combination of a film-forming agent of polymeric type and of a surface-active agent. These agents will be selected in particular from the compounds mentioned above as crystallization inhibitor. In certain embodiments of the invention, film-forming agents of polymeric type include the various grades of polyvinylpyrrolidone, polyvinyl alcohols, polyethylene glycols and copolymers of vinyl acetate and of vinylpyrrolidone. In one embodiment, surface-active agents include those made of non-ionic surfactants, including polyoxyethylenated esters of sorbitan and polyoxyethylenated derivatives of castor oil, and in particular the various grades of polysorbate, for example Polysorbate 80.

The film-forming agent and the surface-active agent can in particular be incorporated in similar or identical amounts within the limit of the total amounts of crystallization inhibitor mentioned elsewhere.

Alternative or additional organic solvents which can be used in the invention include acetyltributyl citrate, fatty acid esters such as the dimethyl ester, diisobutyl adipate, acetone, acetonitrile, benzyl alcohol, butyl diglycol, dimethylacetamide, dimethylformamide, dimethylsulfoxide (DMSO), diethyl sebacate, dimethyl isosorbide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, ethylene glycol; glycol esters including ethylene glycol monoethyl ether acetate, ethylene glycol monobutyl ether acetate, ethylene glycol monomethyl ether acetate, and the like; and diethyl phthalate, or a mixture of at least two of these solvents.

In addition, mention may be made in particular of other possible ingredients such as plant oils: soybean oil, groundnut oil, castor oil, corn oil, cotton oil, olive oil, grape seed oil, sunflower oil, etc.; mineral oils such as petrolatum, paraffin, silicone, etc.; aliphatic or cyclic hydrocarbons or alternatively, for example, medium-chain (C8 to C12 in particular) triglycerides.

An emollient and/or spreading and/or film-forming agent may additionally be added, this agent being selected in particular from: polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils, in particular polydimethylsiloxane (PDMS) oils, for example those containing silanol functionalities, or a 45V2 oil, anionic surfactants such as alkaline stearates, in particular sodium, potassium or ammonium stearates; calcium stearate, triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula $N^+R'R''R'''R''''$, $Y^-$ in which the radicals R', R", R'" and R"" are optionally hydroxylated hydrocarbon radicals and Y is an anion of a strong acid such as the halide, sulphate and sulphonate anions; cetyltrimethylammonium bromide is among the cationic surfactants which can be used, amine salts of formula $N^+HR'''R'''R''''$, $Y^-$ in which the radicals the R", R'" and R"" are optionally hydroxylated hydrocarbon radicals and $Y^-$ is as defined above; octadecylamine hydrochloride is among the cationic surfactants which can be used, nonionic surfactants such as sorbitan esters, which are optionally polyoxyethylenated, in particular polysorbate 80, polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as the substituted lauryl compounds of betaine; or a mixture of at least two of these agents. The emollient may be used in a proportion of from 0.1 to 10%, in particular from 0.25 to 5%, by volume.

In some embodiments, the liquid carrier will contain an organic solvent and optionally an organic co-solvent. In one embodiment, the organic solvent for the liquid carrier vehicle will have a dielectric constant of between about 10 and about 35. In another embodiment, the organic solvent will have a dielectric constant of between about 20 and about 30, the content of this solvent in the overall composition representing the remainder to 100% of the composition. It is well within the skill level of the practitioner to select a suitable solvent on the basis of these parameters.

In some embodiments, the organic co-solvent for the liquid carrier vehicle will have a boiling point of less than about 100° C. In another embodiment, the organic co-solvent will have a boiling point of less than about 80° C., and will have a dielectric constant of between about 10 and about 40. In still another embodiment, the organic co-solvent will have a dielectric constant of between about 20 and about 30. This co-solvent can advantageously be present in the composition according to a weight/weight (w/w) ratio with respect to the solvent of between about 1/15 and about 1/2. In one embodiment, the co-solvent will be volatile in order to act in particular as drying promoter and is miscible with water and/or with the solvent. Again, it is well within the skill level of the practitioner to select a suitable solvent on the basis of these parameters.

The organic solvent for the liquid carrier includes the commonly acceptable organic solvents known in the formulation art. These solvents may be found, for example, in Remington Pharmaceutical Science, 16th Edition (1986). These solvents include, for example, acetone, ethyl acetate, methanol, ethanol, isopropanol, dimethylformamide or dichloromethane. Those solvents which are suitable for topical application are preferred.

In another embodiment, the subject matter disclosed herein is directed to a solvent system comprising A) NMP and B) a glycol, glycol ether, glycol ester, fatty acid ester or neutral oil, wherein the N-methyl pyrrolidone and glycol, glycol ether, glycol ester, fatty acid ester or neutral oil are present in a weight:weight ratio of from about 1:1.8 to about 1:2.8, glycol, glycol ether, glycol ester, fatty acid ester or neutral oil to NMP, wherein dissolved in the solvent system are two active agents selected from one N-arylpyrazole and one pyrethroid. In one such embodiment, the present subject matter is directed to a formulation comprising, one pyrethroid in a concentration of from about 30% w/w to about 55% w/w; one N-arylpyrazole in a concentration of from about 2% w/w to about 10% w/w; and A) glycol, glycol ether, glycol ester, fatty acid ester or neutral oil and B) NMP, wherein the glycol, glycol ether, glycol ester, fatty acid ester or neutral oil and NMP are present in a weight:weight ratio of from about 1:1.8 to about 1:2.8, glycol, glycol ether, glycol ester, fatty acid ester or neutral oil to NMP.

In another embodiment, the formulation comprises one pyrethroid in an concentration of at least about 40% w/w; one N-arylpyrazole in a concentration of at least about 5% w/w; and A) glycol, glycol ether, glycol ester, fatty acid ester or neutral oil and B) NMP, wherein the glycol, glycol ether, glycol ester, fatty acid ester or neutral oil and NMP are present in a weight:weight ratio of from about 1:1.8 to about 1:2.8 or about 1:2.0 to about 1:3.5, glycol, glycol ether, glycol ester, fatty acid ester or neutral oil to NMP.

In another embodiment, the formulation comprises one pyrethroid in an concentration of at least about 40% w/w; one N-arylpyrazole in a concentration of at least about 5% w/w; and A) glycol, glycol ether, glycol ester, fatty acid ester or neutral oil and B) NMP, wherein the glycol, glycol ether, glycol ester, fatty acid ester or neutral oil and NMP are present in a weight:weight ratio of from about 1:2.0 to about 1:3.0, glycol, glycol ether, glycol ester, fatty acid ester or neutral oil to NMP.

In another embodiment, the formulation comprises one pyrethroid in an concentration of at least about 40% w/w; one N-arylpyrazole in a concentration of at least about 5% w/w; and A) glycol, glycol ether, glycol ester, fatty acid ester or neutral oil and B) NMP, wherein the glycol, glycol ether, glycol ester, fatty acid ester or neutral oil and NMP are present in a weight:weight ratio of from about 1:2.5 to about 1:3.5, glycol, glycol ether, glycol ester, fatty acid ester or neutral oil to NMP.

In another embodiment, the formulation comprises one pyrethroid in an concentration of at least about 40% w/w; one N-arylpyrazole in a concentration of at least about 5% w/w; and A) glycol, glycol ether, glycol ester, fatty acid ester or neutral oil and B) NMP, wherein the glycol, glycol ether, glycol ester, fatty acid ester or neutral oil and NMP are present in a ratio of from about 1:2.5 to about 1:3.0, glycol, glycol ether, glycol ester, fatty acid ester or neutral oil to NMP.

In specific aspects of this embodiment, the present subject matter is directed to a pesticidal composition comprising: from about 2% (w/w) to about 15% (w/w) N-arylpyrazole; from about 30% (w/w) to about 55% (w/w) pyrethroid; A) a glycol, glycol ether, glycol ester, fatty acid ester or neutral oil, and B) NMP, wherein said a glycol, glycol ether, glycol ester, fatty acid ester or neutral oil, and NMP are present in a weight:weight ratio of about 1:1.8 to about 1:2.8 or about 1:2.0 to about 1:3.5, about 1:2.0 to about 1:3.0, about 1:2.5 to about 1:3.5 or about 1:2.5 to about 1:3.0, glycol, glycol ether, glycol ester, fatty acid ester or neutral oil to NMP; and optionally an antioxidant.

A useful concentration of N-arylpyrazole in the composition is from about 2% (w/w) to about 15% (w/w). In another embodiment, the concentration of the N-arylpyrazole is from about 3% (w/w) to about 10% (w/w) or about 4% (w/w) to about 8% (w/w). In still another embodiment, the concentration of the N-arylpyrazole is about 6% (w/w).

A useful concentration of the pyrethroid in the compositions of the invention is from about 35% (w/w) to about 50% (w/w). In another embodiment, the pyrethroid is present at a concentration of from about 40% (w/w) to about 48% (w/w). In yet another embodiment, the concentration of the pyrethroid is from about 42% (w/w) to about 47% (w/w). In another embodiment, the concentration of the pyrethroid in the composition is about 45% (w/w).

N-Arylpyrazoles and their parasiticidal and acaricidal activity are known from US 20060014802 A1, WO2005090313 A1, FR2834288 A1, WO9828277, U.S. Pat. No. 6,069,157, WO0031043, DE19824487, WO9804530, WO9962903, EP0933363, EP0911329, WO9856767, U.S. Pat. No. 5,814,652, WO9845274, WO9840359, WO9828279, WO9828278, DE19650197, WO9824767, EP0846686, EP0839809, WO9728126, EP0780378, GB2308365, U.S. Pat. No. 5,629,335, WO9639389, U.S. Pat. No. 5,556,873, EP0659745, U.S. Pat. No. 5,321,040, EP0511845, and EP0234119, EP0295117, and WO 98/24769. These references are hereby incorporated herein in their entirety.

Pyrethroids likewise have a relatively broad parasiticidal action, and some representatives may also show good acaricidal effects. As discussed above, the different physicochemical properties of the materials used require special formulations. However, the solvent system described herein has been shown to solubilize a high concentration of permethrin in combination with fipronil.

In some embodiments the compositions comprising a combination of N-arylpyrazoles and pyrethroids may contain one or more of a cyanopyrethroid (for example flumethrin), a type-1 pyrethroid (for example permethrin) or non-ester pyrethroid (etofenprox) type. In other embodiments, the compositions may include one or more of the pyrethroids α-cyanopyrethroids (for example alpha-cypermethrin, cyfluthrin, beta-cyfluthrin, cyhalothrin, cypermethrin, deltamethrin, fenvalerate, flucythrinate, flumethrin, tau-fluvalinate); type-1 pyrethroids (for example allethrin, bioallethrin, permethrin, phenothrin, resmethrin, tetramethrin, transfluthrin); and non-ester pyrethroids (for example etofenprox, halfenprox, silafluofen).

It is furthermore also possible to use the active compounds in the form of their solvates, in particular hydrates. Solvates are to be understood as meaning both the solvates, in particular hydrates, of the active compounds themselves and the solvates, in particular hydrates, of their salts.

Also contemplated are the pharmaceutically or veterinarily acceptable acid or base salts, where applicable, of the active compounds provided for herein. The term "acid"

contemplates all pharmaceutically or veterinarily acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinarily acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are acetic acid, carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tartaric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid, lactobionic acid, methanesulfonic acid, 4-toluenesulphonic acid, galacturonic acid, embonic acid, glutamic acid or aspartic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

In one embodiment, the liquid carrier may also comprise a microemulsion. Microemulsions are also well suited as the liquid carrier vehicle. Microemulsions are quaternary systems comprising an aqueous phase, an oily phase, a surfactant and a co-surfactant. They may be translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

The oily phase can in particular be formed from mineral or vegetable oils, from unsaturated polyglycosylated glycerides or from triglycerides, or alternatively from mixtures of such compounds. The oily phase may comprise triglycerides including medium-chain triglycerides, for example C8-C10 caprylic/capric triglyceride. In some embodiments the oily phase will represent, in particular, in a concentration of about 2 to about 15%, about 7 to about 10%, or from about 8 to about 9%, v/v of the microemulsion.

In some embodiments, the aqueous phase includes, for example water or glycol derivatives, such as propylene glycol, glycol ethers, polyethylene glycols or glycerol. Propylene glycol, diethylene glycol monoethyl ether and dipropylene glycol monoethyl ether are especially preferred. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolized C8-C10 glycerides or polyglyceryl-6 dioleate. In addition to these surfactants, the co-surfactants include short-chain alcohols, such as ethanol and propanol.

Some compounds are common to the three components discussed above, e.g., aqueous phase, surfactant and co-surfactant. However, it is well within the skill level of the practitioner to use different compounds for each component of the same formulation.

In one embodiment, the co-surfactant to surfactant ratio will be from about ½ to about ½. In another embodiment, the concentration of surfactant will be from about 25 to about 75% v/v and the concentration of the co-surfactant will be from about 10 to about 55% v/v in the microemulsion.

Likewise, the co-solvents are also well known to a practitioner in the formulation art. In some embodiments, co-solvents are those that promote drying and include, for example, absolute ethanol, isopropanol (2-propanol) or methanol.

For the chemical preparation of the products of the invention, a person skilled in the art is regarded as having at his or her disposal, inter alia, the entire contents of "Chemical Abstracts" and of the documents that are cited therein.

Depending on the nature and arrangement of the substituents, the active compounds may, if appropriate, be present in various stereoisomeric forms, in particular as enantiomers and racemates. According to the invention, it is possible to use both the pure stereoisomers and mixtures thereof.

The present subject matter is further described herein by the following non-limiting examples which further illustrate the invention, and are not intended, nor should they be interpreted to, limit the scope of the invention.

EXAMPLES

Example 1: Stable Fly Repellency and Parasiticidal Efficacy in Rats

This study evaluated the effectiveness of a formulation of the invention containing fipronil and permethrin to repel and kill *Stomoxys calcitrans* on rats after a single administration. Rats in the treatment group (Group 2) were treated once on Day 0 with a topical formulation of the invention containing 9.2 (w/w) fipronil and 41.5% (w/w) permethrin in a solvent system containing DMDA and DGME in a ratio of 0.73:1, DMDA to DGME, to deliver a dose of 30 mg/kg permethrin and 6.7 mg/kg fipronil. Rats in Group 3 were treated with a formulation containing permethrin alone to deliver a dose of 30 mg/kg. The two treatment groups were compared with a control group treated with a solvent system placebo.

Flies are exposed to the treated rats for 1 hr., then removed. Dead flies are counted at the end of the exposure period and at 4 hr and 24 hr post-exposure. The fipronil+permethrin group exhibited a very high level of efficacy at all time points measured. Furthermore, the fipronil+permethrin group exhibited significantly higher repellency measured 24 hours after exposure compared with the permethrin only group at the same dose level. This finding is significant because fipronil is not known to have repellent activity.

Figure 6:
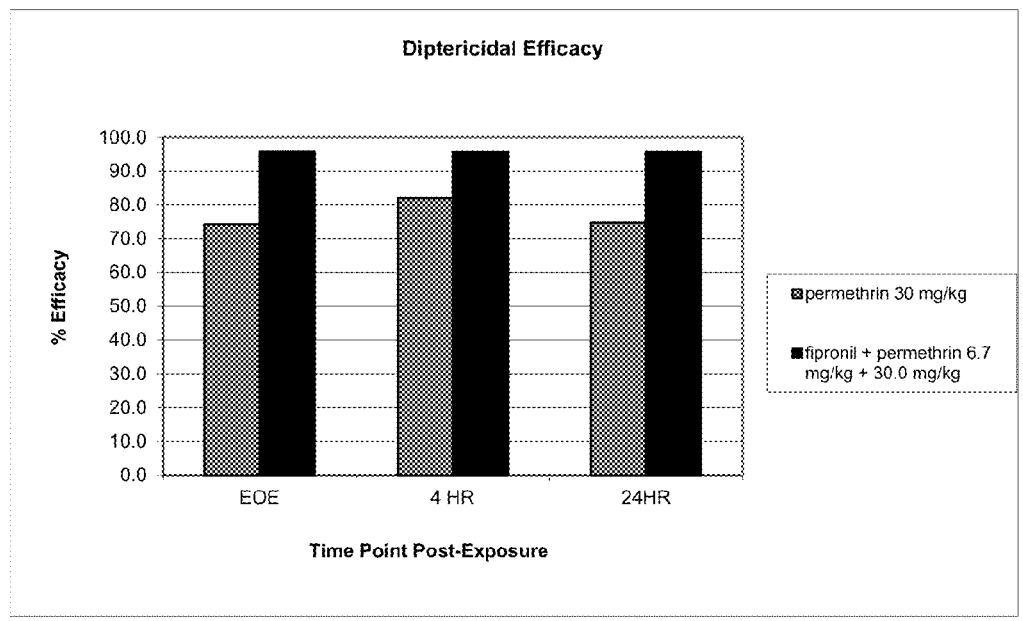
FIG. 6 depicts efficacy against stable fly on rats with a formulation comprising permethrin alone or fipronil/permethrin.
Figure 7:
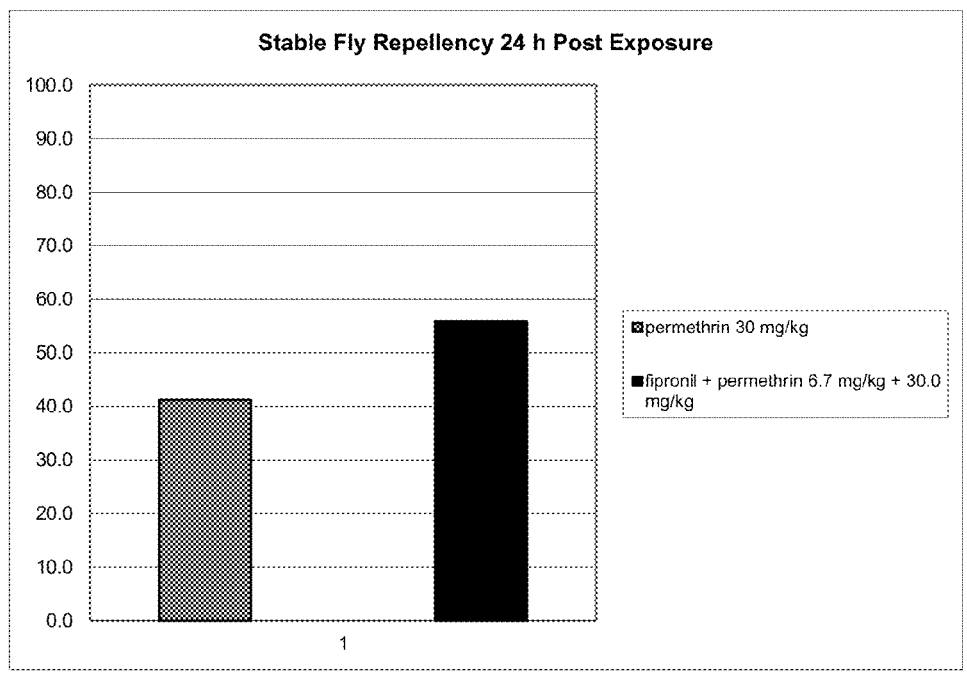
FIG. 7 depicts repellency against stable fly on rats with a formulation comprising permethrin alone or fipronil/permethrin.

The diptericidal efficacy of the formulations is shown in Table 1 and represented in FIG. 6. The data for repellency are shown in Table 2 and are represented in FIG. 7.

TABLE 1

| Treatment | Dose (mg/kg) | EOE % efficacy | 4 hr % efficacy | 24 hr % efficacy |
|---|---|---|---|---|
| Permethrin | 30.0 | 74.2 | 82.0 | 74.7 |
| Fipronil + Permethrin | 6.7 30.0 | 95.8 | 95.7 | 95.6 |

EOE = end of exposure period

TABLE 2

| Treatment | Dose (mg/kg) | % Repellency |
|---|---|---|
| Permethrin | 30.0 | 41.2 |
| Fipronil + Permethrin | 6.7 30.0 | 55.9 |

Example 2: Stable Fly Repellency and Parasiticidal Efficacy on Dogs

This study evaluated the effectiveness of Fipronil+permethrin to repel and kill *Stomoxys calcitrans* on dogs after a single administration.

The fly repellency and parasiticidal activity of a formulation of the invention was evaluated on ten dogs. Dogs were randomly allocated to one of two groups by lottery. Dogs in Group 1 were not treated: Dogs in Group 2 received the topical formulation of the invention containing a combination of fipronil and permethrin described in Table 3 below, administered topically once on Day 0 in a single spot to deliver a dose of approximately 6.70 mg fipronil/kg and 30.15 mg permethrin/kg.

TABLE 3

| Formulation | | |
|---|---|---|
| Ingredient | % w/v | % w/w |
| fipronil | 10 | 9.2 |
| Permethrin | 45 | 41.5 |
| Dimethyl decanamide (DMDA):Diethylene glycol monoethyl ether (DGME) at 0.7:3:1 (w/w) | QS | ~49 |

On Days 1, 14, 21 and 28, dogs were exposed to approximately 100 three to seven day old *S. calcitrans*. After approximately 60 minutes, live flies were aspirated into a vial and dead flies were collected from the cages. After all flies were collected, the live flies were killed and the flies (live and dead) were counted and crushed to determine feeding status (fed vs. unfed). Due to inadequate fly emergence, fly exposures could not be conducted on Day 7

Fly repellency was based on the number of flies that fed in the treated group compared to the control group during each exposure period. Repellency was 99% in treated dogs on Day 1 and was 85.9%, 84.6%, and 61.7% on Days 14, 21, and 28, respectively.

Parasiticidal efficacy was based on the number of live flies in the treated group compared to the control group at the end of each exposure period. Parasiticidal efficacy in treated dogs was 100% on Day 1 and was 98.7%, 95.5%, and 81.3% on Days 14, 21 and 28, respectively. The percent efficacy is listed in Table 3.

In this study, a composition comprising Fipronil+permethrin provided ≥84.6°/0 repellency and ≥95.5% parasiticidal efficacy against *S. calcitrans* (stable flies) for three weeks following treatment.

Summary Data are shown for the fipronil+permethrin composition in Table 4:

TABLE 4

| Summary data | | | | | |
|---|---|---|---|---|---|
| Day | 1 | 7 | 14 | 21 | 28 |
| Repellency | 99.0 | N/A | 85.9 | 84.6 | 61.7 |
| Day | 1 | 7 | 14 | 21 | 28 |
| Parasiticidal Activity | 100.0 | N/A | 98.7 | 95.5 | 81.3 |

Example 3: Crystallization of Actives

Four experimental formulations were prepared with 6% w/w Fipronil and 44.9% w/w permethrin and varying amounts of excipients N-dimethyldecanamide (DMDA) and diethylene glycol monoethyl ether (DGME). The DMDA concentration was varied between 5-20% w/w. These formulations were subjected to different low temperature conditions including −20° C., 4° C., and 10° C.; some samples were seeded with crystals that had grown in previous batches. Crystallization was seen among all the formulations in various conditions.

A DMDA-containing formulation of fipronil and permethrin as described herein was subjected to low temperatures. Some samples were seeded with crystals. Crystals were seen in the DMDA formulation.

Solvents were screened for their compatibility with permethrin and ability to maintain permethrin in solution. The summary of the testing and results are shown in Table 5.

TABLE 5

| Solvent | Crystals |
|---|---|
| Captex 170 (Caprylic/Capric acid Ester) | 100% |
| Oleic acid | 100% |
| Propylene glycol | Immiscible |
| Benzyl benzoate | Less than 5% |
| Propylene carbonate | 100% |
| Glycerol formal | 100% |
| Ethanol | 40% |
| Isopropyl alcohol | Immiscible |
| Diethylene glycol monoethyl ether (DGME) | 100% |
| N,N-Dimethyldecanamide (DMDA) | Less than 5% |

The screening indicates benzyl benzoate and N,N-Dimethyldecanamide are most compatible with permethrin from the experimental set.

In addition to screening solvents for their compatibility with permethrin, several experimental batches were prepared all containing 44.9% w/w permethrin and 6% w/w fipronil. The results of the preparations are shown in Tables 6 and 7.

TABLE 6

| Solvent | Result |
|---|---|
| DGME, ethanol, polysorbate 80, PVP | seeded and unseeded samples stored at 4° C. crystallized 100% within 24 hours |
| N-methylpyrrolidone | seeded and unseeded samples stored at 4° C. have not grown crystals after 5 days |
| Dimethyl Isosorbide/ Diisopropyl adipate | Solution turned hazy after all ingredients added |

TABLE 6-continued

| Solvent | Result |
| --- | --- |
| Dimethyl Isosorbide/Benzyl benzoate | Fipronil was insoluble |
| Triacetin/diisopropyl adipate | Fipronil was insoluble |
| Triacetin/benzyl benzoate | Fipronil was insoluble |

The formulation containing N-methylpyrrolidone has the best physical stability of the set.

TABLE 7

Formulation (% w/w or grams per 100 g of solution) Crystallization on day 8

| Solvent system | | Fipronil | Permethrin | Prepared on | Without seeding | With seeding |
| --- | --- | --- | --- | --- | --- | --- |
| DGME | 24.5 | 6 | 45 | Day 1 | No | Yes |
| Diisopropyl Adipate | 24.5 | | | | | |
| Polysorbate 80 | 3.0 | 6 | 45 | Day 1 | No | Yes |
| DGME | 23.0 | | | | | |
| Diisopropyl Adipate | 23.0 | | | | | |
| DGME | 32 | 6 | 45 | Day 2 | No | Yes |
| Diisopropyl Adipate | 17 | | | | | |
| DMDA | 23.5 | 6 | 45 | Day 3 | No | Yes |
| Diisopropyl Adipate | 25.5 | | | | | |
| DMDA | 16 | 6 | 45 | Day 3 | No | Yes |
| Diisopropyl Adipate | 33 | | | | | |
| NMP | 14.5 | 6 | 45 | Day 4 | No | Yes, very small amounts of crystals |
| Diisopropyl Adipate | 34.5 | | | | | |
| NMP | 49 | 6 | 45 | Day 5 | No | No |
| NMP | 44 | 6 | 45 | Day 5 | No | No |
| Diisopropyl Adipate | 5 | | | | | |
| NMP | 44 | 6 | 45 | Day 5 | No | No |
| Triacetin | 5 | | | | | |

Note:
1) These results are approximate and based on lab screening data.
2) Amount of DGME, DMDA, NMP is approximate and will depend on assay of actives.
3) Assay of all actives is assumed 100% in these experiments and calculations.

Example 4: One Formulation of the Invention Described Fully Herein is Shown in Table 8

TABLE 8

| Ingredient | % w/w | % w/v |
| --- | --- | --- |
| NMP | 35 | 39.4 |
| BHT | 0.10 | 0.11 |
| Fipronil | 6.0 | 6.8 |
| Permethrin | 44.9 | 50.5 |
| MIGLYOL ® 812 | QS (~14) | QS (~15) |

Example 5: Efficacy of Against Fleas (*Ctenocephalides felis*) and Ticks (*Rhipicephalus sanguineus*) on Dogs A study was conducted to evaluate the effectiveness of three different formulations of the invention containing fipronil and permethrin in amounts to deliver doses of ≥6.7 mg/kg and ≥50.3 mg/kg, respectively, compared with a formulation containing permethrin alone in an amount to deliver a dose of ≥50.3 mg/kg.

Five treatment groups of six dogs each were formed. Dogs in Group 1 were untreated. On Day 0 dogs in Groups 2, 3 and 4 received a spot-on formulation of the invention containing 6.0% (w/w) fipronil and 44.9% (w/w) permethrin in different solvent systems. Dogs in Group 5 were treated on Day 0 with a spot-on formulation containing 44.9% (w/w) permethrin alone. The efficacy of the treatments was measured against the control Group 1 for each observation point. The formulation components are shown in Table 9 below.

TABLE 9

| Ingredient | Group 2 (% w/w) | Group 3 (% w/w) | Group 4 (% w/w) | Group 5 (% w/w) |
| --- | --- | --- | --- | --- |
| Fipronil | 6.0 | 6.0 | 6.0 | |
| Permethrin | 44.9 | 44.9 | 44.9 | 44.9 |
| NMP | 35 | 35 | | 35 |
| DGME | QS (~12.5) | | | QS (~18.7) |
| MIGLYOL ® 812 | | QS (~12.4) | | |
| BCA | | | 25 | |
| DMDA | | | QS (~22.6) | |
| BHT | 0.1 | 0.1 | | 0.1 |

All dogs were infested with approximately 100 *C. felis* on Days −1, 8, 15, 22 and 29. Flea counts were performed on Days 1, 9, 16, 23 and 30. All dogs were also infested with approximately 50 *Rhipicephalus sanguineus* on Days −1, 14 and 28. Ticks were thumb-counted on Days 15 and 29 and counted and removed on Days 1, 16 and 30.

The efficacy against fleas was similar for Groups 2, 3 and 4, ranging from 95-100% through Day 30. The efficacy for Group 5 was 51% on Day 1 and reached a peak of 96% on Day 9, then dropped to 13% by Day 30.

The efficacy against ticks at 24 hours after treatment was 69.1%, 89.9%, 94.7% and 70.2% for Groups 2, 3, 4 and 5, respectively. Efficacy against ticks at 24 hours following infestation ranged from 91-99% across all treated groups on Day 15 and from 56-81% on Day 29. Efficacy against ticks at 48 hours after infestation ranged from 96-100% across all treated groups on Day 16 and from 74-85% on Day 30.

Figure 4:
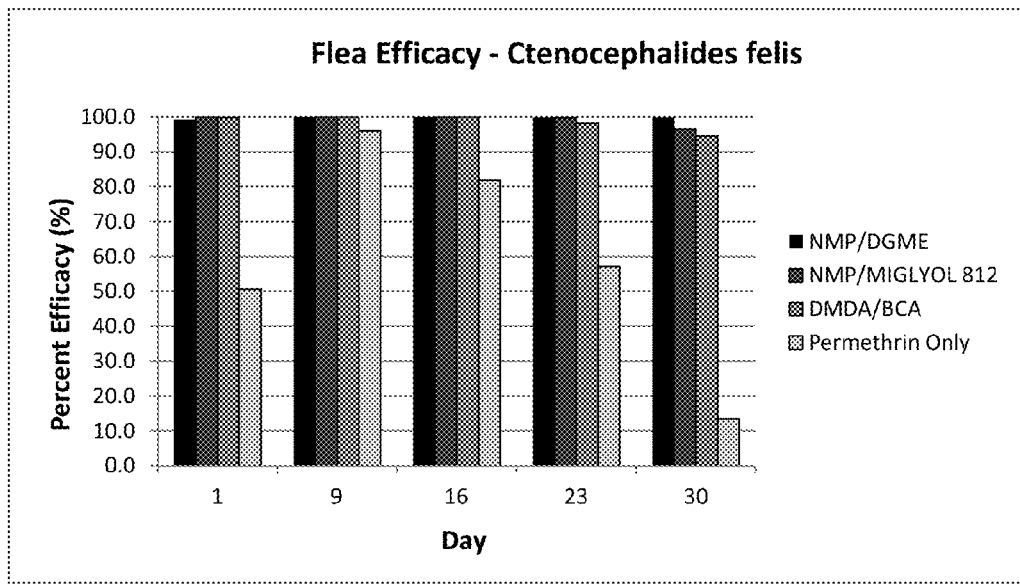
FIG. 4 depicts efficacy against fleas of formulations containing fipronil/permethrin and NMP/DGME, NMP/MIGLYOL® 812 or N,N-dimethyldecanamide (DMDA)/butyl CELLOSOLVE™ acetate (BCA), or permethrin alone. NMP/DGME formulations are more susceptible to fipronil degradation
Figure 5:
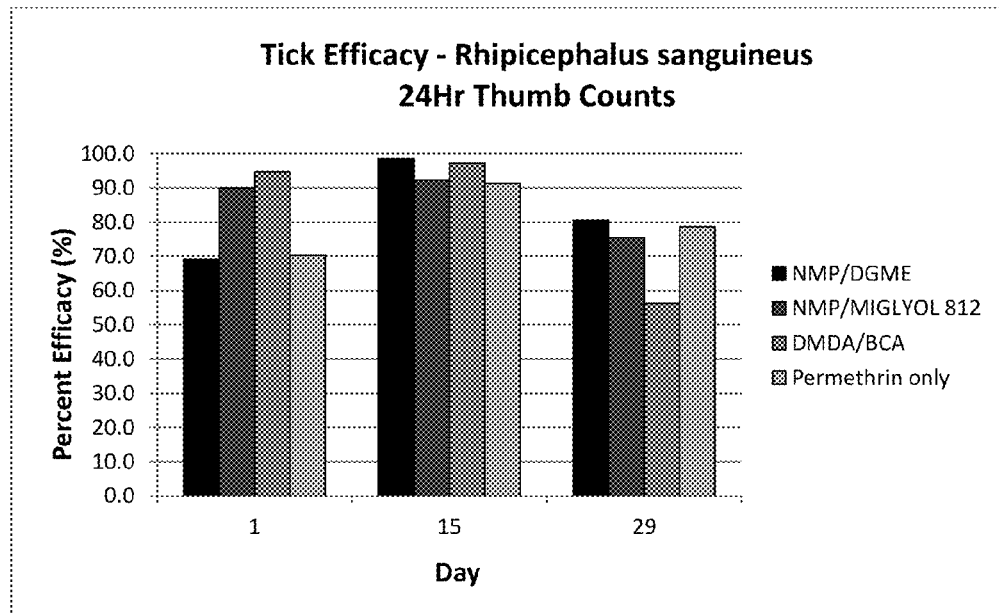
FIG. 5 depicts efficacy against ticks of formulations containing fipronil/permethrin and NMP/DGME, NMP/MIGLYOL® 812 or DMDA/BCA, or permethrin alone.

This study demonstrates that the formulations of the invention provided superior efficacy against *C. felis* and *R. sanguineus* compared to a formulation containing permethrin alone. The efficacy data is also presented in FIGS. 4 and 5.

Example 6: Repellency and Efficacy Against *Phlebotomus perniciosus* Sand Flies on Dogs This study evaluated the effectiveness of two formulations of the invention containing fipronil and permethrin to repel and kill *Phlebotomus perniciosus* on dogs after a single administration.

Following a procedure very similar to that described in Example 2, the repellency and insecticidal efficacy of the formulations was studied. Three treatment groups of five dogs each were formed. Dogs in Group 1 were untreated. Dogs in Groups 2 and 3 were treated once on Day 0 with the formulations of the invention described in Table 10 below to deliver doses of ≥6.7 mg/kg fipronil and ≥50.3 mg/kg permethrin.

TABLE 10

| Ingredient | Group 2 (% w/w) | Group 3 (% w/w) |
| --- | --- | --- |
| Fipronil | 6.0 | 6.0 |
| Permethrin | 44.9 | 44.9 |
| NMP | 35 | 35 |
| DGME | QS (~12.5) | |
| MIGLYO ®L 812 | | QS (~12.4) |
| BCA | | |
| DMDA | | |
| BHT | 0.1 | 0.1 |

Dogs were exposed to eighty (±5) *P. perniciosus* female sand flies on Days 1, 7, 14, 21, 29 and 35. After 60 minutes, sand flies were removed and categorized as live (engorged or non-engorged), dead (engorged or non-engorged). Efficacy was determined by determining the number of dead flies approximately four hours after exposure and on days 2, 8, 15, 22 and 29 approximately twenty four hours after exposure. Repellency was measured by comparing the number of engorged flies (live or dead) in the treatment groups compared with the number of engorged flies in the control group.

The repellency observed for dogs in treatment Group 2 on days 1, 7, 14, 21, 29 and 35 was measured to be 97.0%, 90.1%, 96.0%, 80.0%, 96.4% and 79.6%, respectively. The repellency for dogs in Group 3 on days 1, 7, 14, 21, 29 and 35 was found to be 94.4%, 94.7%, 99.3%, 88.6%, 97.3% and 82.5%, respectively.

The efficacy for Group 2 at 4 hours after exposure on days 1, 7, 14, 21, 29 and 35 was 99.8%, 100.0%, 94.0%, 63.2%, 91.1% and 65.8%, respectively. The efficacy for Group 3 at 4 hours after exposure on days 1, 7, 14, 21, 29 and 35 was 99.6%, 100.0%, 92.3%, 56.3%, 90.6% and 70.0%, respectively.

The efficacy for Group 2 at 24 hours after exposure on days 2, 8, 15, 22, 30 and 36 was 100.0%, 99.4%, 94.4%, 66.3%, 91.7% and 69.6%, respectively. The efficacy for Group 3 at 4 hours after exposure on days 2, 8, 15, 22, 30 and 36 was 99.6%, 100.0%, 92.6%, 58.0%, 93.1% and 70.7%, respectively.

Figure 3:
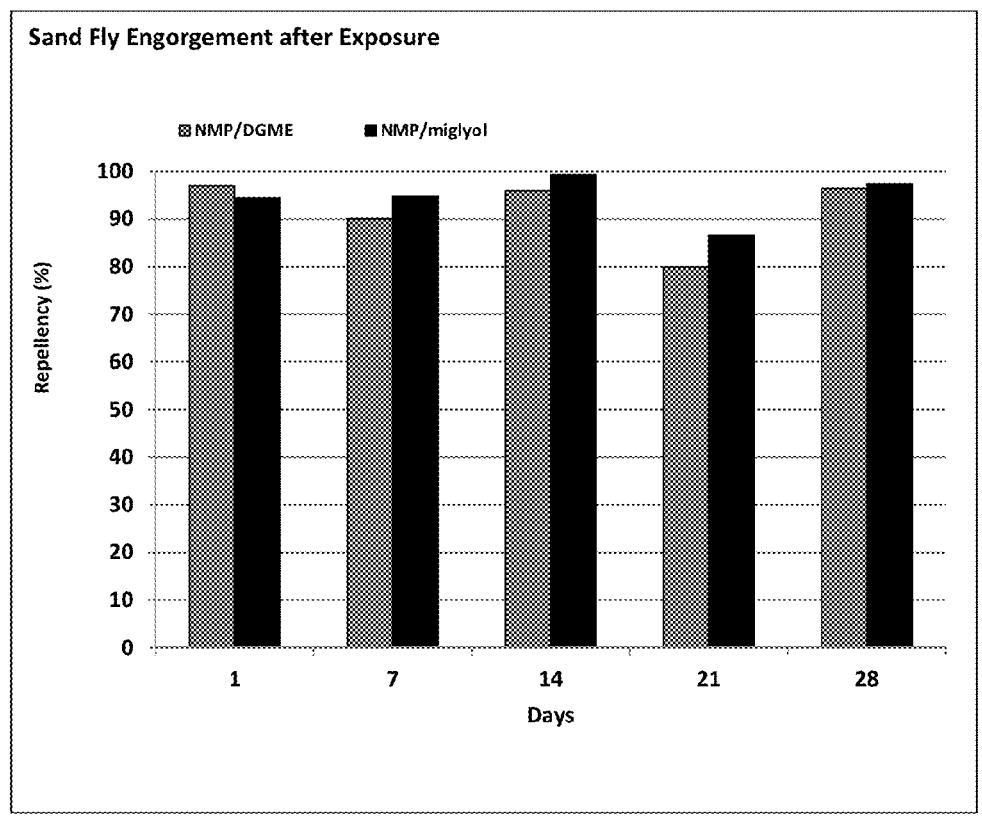
FIG. 3 depicts sand fly repellency of formulations containing fipronil/permethrin and NMP/DGME or NMP/MIGLYOL® 812.

This study demonstrates that the formulations of the invention provide excellent repellency for at least 35 days and excellent insecticidal efficacy for at least 30 days against *Phlebotomus perniciosus* on dogs after a single treatment. The data is also presented in FIG. 3.

Example 7: Repellency and Efficacy Against Stable Flies (*Stomoxys calcitrans*) on Dogs This study was conducted to evaluate the repellency and efficacy of a spot-on formulation of the invention described in Table 8 above comprising a combination of fipronil and permethrin against *Stomoxys calcitrans* stable flies after a single topical administration.

Figure 8:
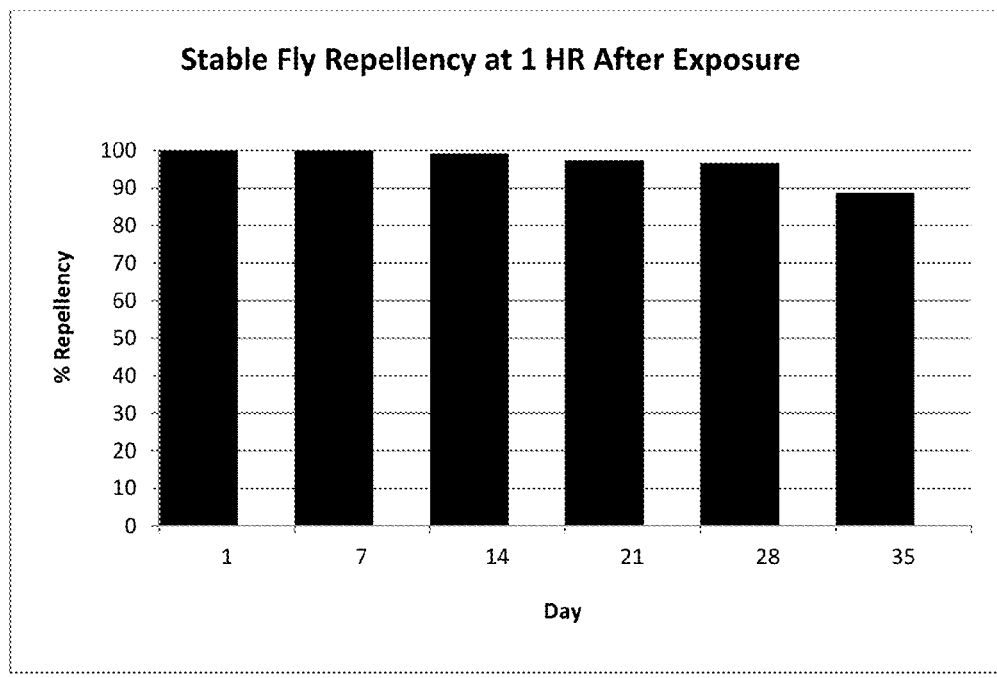
FIG. 8 depicts repellency against stable fly on dogs of a formulation comprising fipronil and permethrin one hour post exposure.
Figure 9:
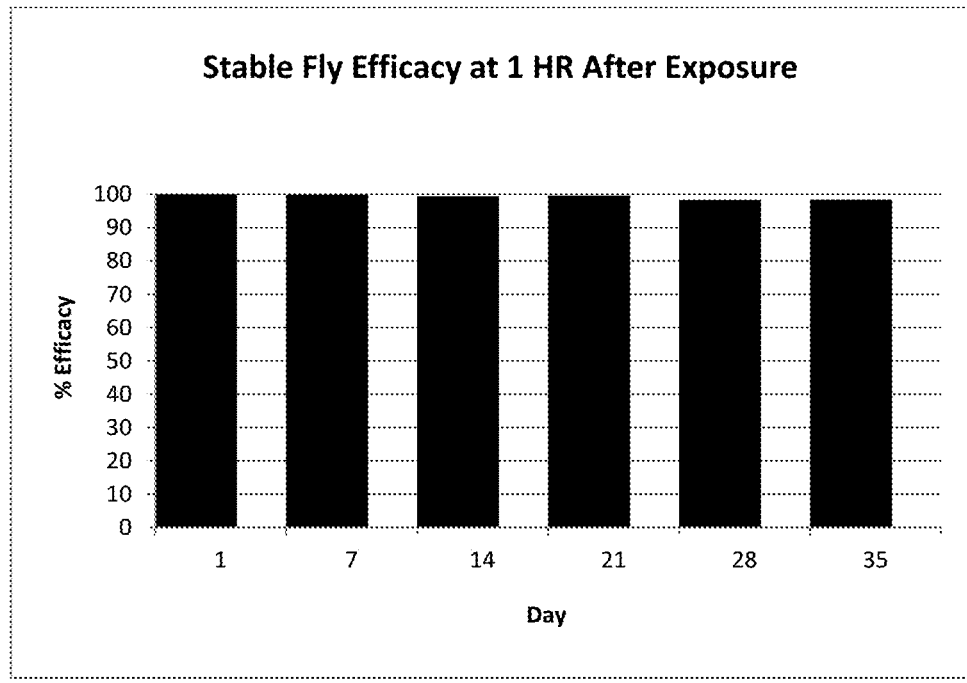
FIG. 9 depicts the efficacy against stable fly on dogs of a formulation comprising fipronil and permethrin one hour post exposure.

Following a procedure very similar to that described in Example 2 above, two groups of eight dogs each were formed. The dogs in Group 1 were untreated and served as a control group. Dogs in Group 2 were treated once on Day 0 with the formulation of Table 8 to deliver doses of 6.8 mg/kg fipronil and 50.5 mg/kg permethrin. Dogs were exposed to approximately 100 stable flies on days 1, 7, 14, 21, 28 and 35 for approximately 60 minutes, after which the flies (both live and dead) were collected and examined to determine feeding status. Repellency of the formulation administered to Group 2 dogs was measured to be 100.0%, 100.0%, 99.2%, 97.3%, 96.6% and 88.7% on days 1, 7, 14, 21, 28 and 35, respectively. The insecticidal efficacy of the formulation applied to Group 2 dogs was measured to be 100.0%, 99.9%, 99.4%, 99.6%, 98.3% and 98.3% on Days 1, 7, 14, 21, 28 and 35 respectively. The repellency and efficacy data is presented in FIGS. 8 and 9.

The very high level of repellency and insecticidal efficacy against *Stomoxys calcitrans* with a duration of action of at least 35 days for the formulation of Example 8 is surprising for a topical formulation comprising permethrin at the dose level applied. For example, Fourie et al. reported that a topical formulation comprising 10% imidacloprid and 50% permethrin (the same concentration of permethrin in the formulation used in the present example) only prevented 82% of *S. calcitrans* from feeding on dogs for 4 weeks after treatment and exhibited an average efficacy of 85.6% over the evaluation period of 29 days. (see "The Efficacy of a Topically Applied Combination of Imidacloprid and Permethrin Against *Stomoxys calcitrans* on Dogs," *Intern. J. Appl. Res. Vet. Med.*, 2006, vol. 4(1), pp. 29-33). In this study, the highest repellency observed over the whole 29 day assessment period was 90.2% 1 day post treatment while the repellency at all other time points were below 90%. The repellency and efficacy exhibited by the formulation of the invention is surprisingly superior to another topical formulation comprising the same concentration of permethrin in combination with a different pesticidal active agent. The superior repellency is particularly surprising because fipronil is not known to have any repellent activity.

Example 8: Repellency Against Mosquitoes (*Culex pipiens*) on Dogs

This study was conducted to evaluate the repellency and efficacy of a spot-on formulation of the invention described in Table 8 above against *Culex pipiens* after a single topical administration.

Following a procedure very similar to that described in Example 2 above, two groups of eight dogs each were formed. The dogs in Group 1 were untreated and served as a control group. Dogs in Group 2 were treated once on Day 0 with the formulation of Table 8 to deliver doses of 6.8 mg/kg fipronil and 50.5 mg/kg permethrin. Dogs were exposed to approximately 100 *Culex pipiens* female mosquitoes per dog on days 1, 7, 14, 21 and 28 for approximately 60 minutes, after which the mosquitoes (both live and dead) were collected and examined to determine feeding status.

Figure 10:
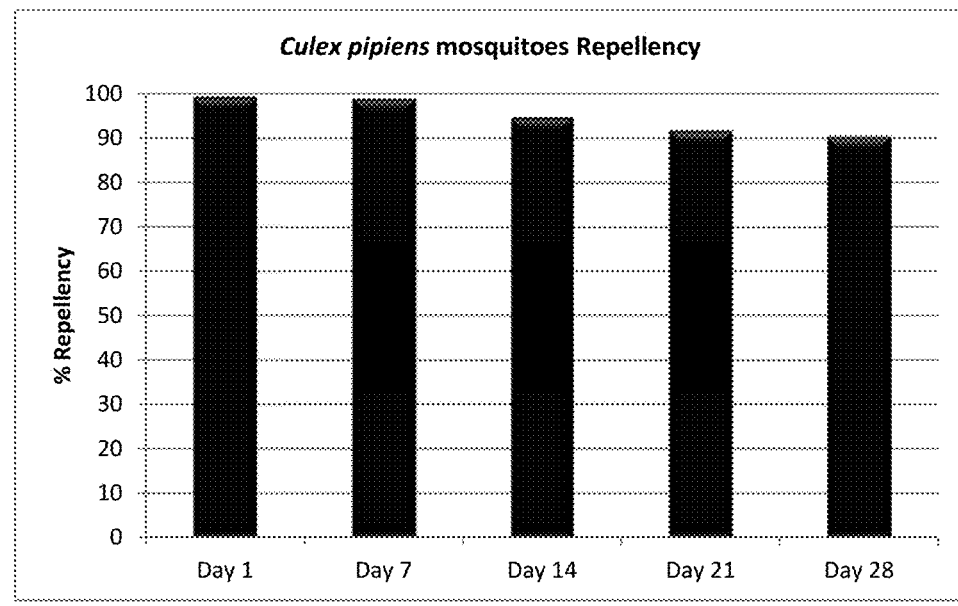
FIG. 10 depicts the repellency against *Culex pipiens* mosquitoes of a formulation comprising fipronil and permethrin one hour post exposure.

Repellency of the formulation administered to Group 2 dogs was measured to be 99.4%, 98.9%, 94.7%, 91.7% and 90.4% for days 1, 7, 14, 21 and 28, respectively. The repellency data is presented in FIG. 10.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

Having thus described in detail certain embodiments of the present invention, it is to be understood that the invention defined by the above paragraphs is not to be limited to particular details set forth in the above description as many apparent variations thereof are possible without departing from the spirit or scope of the present invention.

That which is claimed:

1. A topical composition for the treatment and prevention of an ectoparasitic infestation comprising:
   from about 2% (w/w) to about 15% (w/w) fipronil;
   from about 30% (w/w) to about 55% (w/w) permethrin;
   from about 1% (w/w) to about 15% (w/w) of an insect growth regulator; and a neutral oil(s) and N-methyl pyrrolidone, wherein said neutral oil(s) is a triglyceride of $C_8$ to $C_{10}$ fatty acids, and wherein said neutral oil(s) and N-methyl pyrrolidone are present in a weight:weight ratio of from about 1:2.0 to about 1:3.0, neutral oil(s) to N-methyl pyrrolidone, wherein the term about encompasses variations of ±5%, from the specified amount.

2. The composition of claim 1, wherein said fipronil is present in a concentration of from about 4% (w/w) to about 8% (w/w).

3. The composition of claim 1, wherein said fipronil is present at a concentration of about 6% (w/w).

4. The composition of claim 1, wherein said permethrin is present in a concentration of from about 35% (w/w) to about 50% (w/w).

5. The composition of claim 1, wherein said permethrin is present in a concentration of from about 40% (w/w) to about 48% (w/w).

6. The composition of claim 1, wherein said permethrin is present at a concentration of about 45% (w/w).

7. The composition of claim 1, wherein said fipronil is present at a concentration of about 6.0% (w/w) and said permethrin is present at a concentration of about 45% (w/w).

8. The composition of claim 1, wherein said neutral oil(s) is present in a concentration of about 12% (w/w) to about 14% (w/w) and said N-methyl pyrrolidone is present in a concentration of about 35% (w/w).

9. The composition of claim 1, wherein said neutral oil(s) and said N-methyl pyrrolidone are present in a weight:weight ratio of about 1:2.5 to about 1:3.0, neutral oil(s) to N-methyl pyrrolidone.

10. The composition of claim 1, wherein said neutral oil(s) and said N-methyl pyrrolidone are present in a weight:weight ratio of about 1:2.2 to about 1:2.4, neutral oil(s) to N-methyl pyrrolidone.

11. The composition of claim 1, wherein said neutral oil(s) and said N-methyl pyrrolidone are present in a weight:weight ratio of about 1:2.5 to about 1:2.8, neutral oil(s) to N-methyl pyrrolidone.

12. The composition of claim 1, wherein said neutral oil(s) is a triglyceride of fractionated plant fatty acids having chain lengths of $C_8$ and $C_{10}$.

13. The composition of claim 1, further comprising an antioxidant.

14. The composition of claim 13, wherein said antioxidant is butylated hydroxytoluene.

15. The topical composition of claim 1, wherein the insect growth regulator is a juvenile hormone mimic selected from the group consisting of azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one.

16. The topical composition of claim 15, wherein the juvenile hormone mimic is methoprene.

17. The topical composition of claim 16, wherein methoprene is present at a concentration of from about 5% (w/w) to about 15% (w/w).

18. The topical composition of claim 15, wherein the juvenile hormone mimic is pyriproxyfen.

19. The topical composition of claim 18, wherein pyriproxyfen is present in a concentration of from about 0.01% (w/w) to about 10% (w/w).

20. The topical composition of claim 19, wherein pyriproxyfen is present in a concentration of from about 0.1% (w/w) to about 2% (w/w).

21. The composition of claim 20, comprising
   about 6% (w/w) fipronil;
   about 45% (w/w) permethrin;
   about 2% (w/w) pyriproxyfen;
   about 12% to about 14% (w/w) of triglycerides of fractionated plant fatty acids having chain lengths of $C_8$ and $C_{10}$ (w/w);
   about 35% (w/w) N-methyl pyrrolidone; and
   about 0.1% (w/w) butylated hydroxytoluene.

22. The topical composition of claim 1, wherein the insect growth regulator is a chitin synthesis inhibitor selected from the group consisting of chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

23. A spot-on composition, comprising
   from about 2% (w/w) to about 15% (w/w) fipronil;
   from about 30% (w/w) to about 55% (w/w) permethrin;

from about 1% to about 15% (w/w) pyriproxyfen or (S)-methoprene;

and a neutral oil(s) and N-methyl pyrrolidone, wherein said neutral oil(s) is a triglyceride of $C_8$ to $C_{10}$ fatty acids, and wherein said neutral oil(s) and N-methyl pyrrolidone are present in a weight:weight ratio of from about 1:2.0 to about 1:3.0, wherein said composition is a liquid having a volume of from about 1 mL to about 10 mL, wherein the term about encompasses variations of ±5%, from the specified amount.

24. The composition of claim 1 or 23, further comprising fipronil sulfone below about 3.5% by area relative to the peak area for fipronil as measured by HPLC at about three months after formulation.

25. The composition of claim 1 or 23, further comprising fipronil sulfone wherein said amount of fipronil sulfone at about three months after formulation has not increased by more than 50% of the original amount of said fipronil sulfone present at the time of formulation.

26. A method for the treatment and/or protection of a parasite infestation in an animal, comprising administering an effective amount of the composition of claim 1 to the animal.

27. The method of claim 26, wherein said administering comprises contacting the coat and/or skin of said animal with said composition.

* * * * *